(12) United States Patent
Ludwig et al.

(10) Patent No.: US 10,251,391 B2
(45) Date of Patent: *Apr. 9, 2019

(54) OXIDIZING ALKALINE BIODECONTAMINATION GEL AND SURFACE BIODECONTAMINATION METHOD USING SAID GEL

(71) Applicant: COMMISSARIAT À L'ÉNERGIE ATOMIQUE ET AUX ÉNERGIES ALTERNATIVES, Paris (FR)

(72) Inventors: Amélie Ludwig, Salon de Provence (FR); Frédéric Goettmann, Les Angles (FR); Fabien Frances, Rousson (FR); Charline Legoff, Pont Saint Esprit (FR); Valérie Tanchou, Orange (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 239 days.

This patent is subject to a terminal disclaimer.

(21) Appl. No.: 14/780,756

(22) PCT Filed: Mar. 27, 2014

(86) PCT No.: PCT/EP2014/056183
§ 371 (c)(1),
(2) Date: Sep. 28, 2015

(87) PCT Pub. No.: WO2014/154818
PCT Pub. Date: Oct. 2, 2014

(65) Prior Publication Data
US 2016/0050911 A1     Feb. 25, 2016

(30) Foreign Application Priority Data
Mar. 29, 2013 (FR) ...................................... 13 52907

(51) Int. Cl.
*A01N 25/04* (2006.01)
*A61L 2/22* (2006.01)
(Continued)

(52) U.S. Cl.
CPC ............. *A01N 25/04* (2013.01); *A01N 59/00* (2013.01); *A61L 2/22* (2013.01); *A61L 2/23* (2013.01)

(58) Field of Classification Search
CPC ............ A61L 2/22; A05N 25/04; A01N 25/04
(Continued)

(56) References Cited

U.S. PATENT DOCUMENTS

| 6,294,511 B1 | 9/2001 | Argo et al. |
| 6,455,751 B1 | 9/2002 | Hoffman et al. |

(Continued)

FOREIGN PATENT DOCUMENTS

| FR | 2827530 A1 | 1/2003 |
| FR | 2891470 A1 | 4/2007 |

(Continued)

OTHER PUBLICATIONS

English translation of International Publication No. FR 2962046 provided by the European Patent Office, Espacenet.com: Frederric Cuer, Biological Decontamination Gel, and Method for Decontaminating Surfaces Using Said Gel, Jan. 6, 2012.*

(Continued)

*Primary Examiner* — Kevin Joyner
(74) *Attorney, Agent, or Firm* — Pearne & Gordon LLP

(57) ABSTRACT

A biological decontamination gel is provided, consisting of a colloidal solution comprising 5% to 30% by mass, preferably 5% to 25% by mass, still more preferably 8% to 20% by mass based on the mass of the gel, of at least one inorganic viscosifying agent; an active biological decontamination agent consisting of the combination of a mineral (Continued)

base selected from hydroxides of alkaline metals, hydroxides of earth alkaline metals, and mixtures thereof, and of an oxidizing agent stable in a basic medium selected from permanganates, persulfates, ozone, hypochlorites, and mixtures thereof; the mineral base being present in an amount from 0.05 to 10 mol/L of gel, preferably in an amount from 0.1 to 5 mol/L of gel, and the oxidizing agent stable in a basic medium being present in an amount from 0.05 to 5 mol/L of gel, preferably from 0.1 to 2 mol/L of gel; optionally 0.1% to 2% by mass based on the mass of the gel, of at least one surfactant; and the balance of solvent; and the gel not containing any super-absorbent polymer.

30 Claims, 12 Drawing Sheets

(51) Int. Cl.
*A61L 2/23* (2006.01)
*A01N 59/00* (2006.01)

(58) Field of Classification Search
USPC .......................................................... 424/665
See application file for complete search history.

(56) References Cited

U.S. PATENT DOCUMENTS

| | | | |
|---|---|---|---|
| 8,636,848 | B2 | 1/2014 | Faure et al. |
| 2005/0061357 | A1 | 3/2005 | Steward et al. |
| 2006/0241002 | A1 | 10/2006 | Rogozinski |
| 2009/0197790 | A1* | 8/2009 | Sengupta ............ C11D 3/0047 510/372 |
| 2012/0021068 | A1* | 1/2012 | Barness ............... C11D 3/3953 424/661 |
| 2013/0023713 | A1 | 1/2013 | Labe et al. |
| 2013/0171024 | A1 | 7/2013 | Cuer et al. |

FOREIGN PATENT DOCUMENTS

| | | | |
|---|---|---|---|
| FR | 2962046 | A1 | 1/2012 |
| JP | 2000-212598 | A | 8/2000 |
| JP | 2000515922 | A | 11/2000 |
| JP | 2012-219267 | A | 11/2012 |
| RU | 2449392 | C2 | 4/2012 |
| WO | 1998-004665 | A1 | 2/1998 |
| WO | 2004108170 | A1 | 12/2004 |
| WO | WO-2010037809 | A1 * | 4/2010 ........... C04B 41/009 |
| WO | 2010079487 | A2 | 7/2010 |
| WO | 2012001046 | A1 | 1/2012 |
| WO | 2014154817 | A1 | 10/2014 |

OTHER PUBLICATIONS

English Translation of International Publication No. WO 2010/037809 A1 provided by espacenet.com; Cuer; Process for the Electrokinetic Decontamination of a Porous Solid Medium; Apr. 8, 2010.*

Harper, B., et al., "A Comparison of Decontamination Technologies for Biological Agents on Selected Commercial Surface Materials", "Domestic Preparedness", Apr. 2001, Publisher: U.S. Army Soldier and Biological Chemical Command.

Co-pending Unpublished U.S. Appl. No. 14/647,782, filed Nov. 29, 2013.

Co-pending Unpublished U.S. Appl. No. 14/769,846, filed Nov. 8, 2013.

Translation of Japanese Patent Office action for JP2016-504680 dated Jan. 23, 2018.

* cited by examiner

OXIDIZING ALKALINE BIODECONTAMINATION GEL AND SURFACE BIODECONTAMINATION METHOD USING SAID GEL

CROSS-REFERENCE TO RELATED APPLICATIONS

This application is a U.S. national phase under the provisions of 35 U.S.C. § 371 of International Patent Application No. PCT/EP14/56183 filed Mar. 27, 2014, which in turn claims priority of French Patent Application No. 1352907 filed Mar. 29, 2013. The disclosures of such international patent application and French priority patent application are hereby incorporated herein by reference in their respective entireties, for all purposes.

TECHNICAL FIELD

The object of the present invention is an oxidizing alkaline gel for biological decontamination with may be used for decontaminating surfaces.

The present invention further relates to a method for biological decontamination of surfaces using this gel.

The invention applies to the decontamination of polluted, contaminated surfaces by biological agents.

The method according to the invention may be applied to any kinds of surface such as metal surfaces, plastic surfaces, glassy material surfaces, surfaces in cement materials such as slurries, mortars and concretes; brick surfaces; plaster surfaces; surfaces in ceramics; and surfaces in natural or artificial stone. These surfaces may be either painted or not.

The technical field of the invention is that of biological decontamination of contaminated surfaces notably with biological species and notably toxic biological species, for example of the type: endospores, toxins, viruses, with view to removing these species, the presence of which on these surfaces is not desired, from these surfaces.

STATE OF THE PRIOR ART

Since a few decades, the succession of chemical terrorist acts and more recently biological acts, for example the attacks with sarin gas in the metro of Tokyo in 1995 and the anthrax in the letter bombs of the US Postal Service in the United States in 2001, has incited many countries to develop strategic means, so-called "post-event" intervention means, for efficiently reacting to the consequences of possible terrorist attacks using biological, chemical or radiological agents.

Essentially of a chemical nature at the beginning of the XXth century, the threatening agents have evolved towards weapons of greater impact, simpler to apply and especially non-detectable before occurrence of the first symptoms on the body.

Fear is therefore today rather directed to terrorist attacks of the biological type, notably with contagious biological agents of class A, which may easily be disseminated, and which cause significant morbidity and mortality. The pathogenic biological species such as *Bacillus anthracis* (anthrax or charbon) or further the bacterium *Yersinia pestis* (plague) are considered as the agents for which the probability of use is the strongest.

Assuming such an event, the priority for the authorities is to limit the effects of the attack on the civilian population by rapidly decontaminating the exposed, notably civilian infrastructures, in order to avoid propagation of toxic species through technical installations and equipment, such as ventilation conduits and waste water discharge conduits, and to restore as quickly as possible the buildings to their use without any persistence of a risk to being exposed to the toxic species.

This decontamination may pass through two successive steps:
  neutralization, or even destruction of the toxic species, when this is possible.
  transfer of the toxic species towards a solid or liquid phase allowing its removal.

Generally, sanitation techniques for materials contaminated with a biological contamination consist in putting a liquid containing a biocidal agent in contact with the contaminated surfaces. The application of the biocidal solution is generally achieved by spraying or by washing either coupled or not with a mechanical effect such as brushing.

An overview of these techniques is provided in documents FR-A1-2962046 and WO-A1-2012/001046 [1].

It is notably indicated therein that the decontamination products, which appear as a gel, generate a solid waste and thus gives the possibility of doing without the use of liquid solutions for sanitizing rooms with large surfaces and complex geometries.

These gels are generally applied by spraying them on the surface to be decontaminated.

After a period of contact of the gel with the surface to be decontaminated, equivalent to the period of evaporation of the solvent, the obtained dry waste is removed by brushing and/or suction. The major benefit of these methods is their capability of treating large surfaces and uneven geometries.

Thus, document [2] describes a gel composition containing oxidizing agents for chemical or biological decontamination of contaminated areas. This composition is prepared by adding thickeners or gelling agents as colloids to a solution of an oxidizing agent in order to form a viscous colloidal gel.

This solution may be an aqueous or organic solution.

The thickeners or gelling agents may be selected from among silica, alumina, aluminosilicates, mixtures of silica and alumina, and clays such as smectite.

The oxidizing agents are notably sodium hypochlorite, ammonium persulfate, or hydrogen peroxide.

It is mentioned that the gel may be basic with a pH greater than or equal to 12, but no detail is provided as to the nature of the base added for obtaining such a pH.

It is indicated that these gels may be used for removing biological agents such as micro-organisms like bacteria, fungi, viruses, and spores, or chemical agents such as neurotoxic gases.

The gels are then sprayed on the surfaces to be treated and then recovered by suction after drying.

It is specified that an oxidizing gel containing potassium peroxymonosulfate and 15% of silica Cab-O-Sil® EH-5 as a gelling agent, destroys the chemical agents "Mustard", "VX" and "GD" within the time required for bringing the gel to dryness and that the *Bacillus globigii* (BG), a simulator of Anthrax is also destroyed partly by this gel.

The gelled formulations developed by the Lawrence Livermore National Laboratory under the name of L-Gels such as L-Gel 115, and L-Gel 200 are similar to the formulations developed in document [2] and are applied with the so-called "L-Gel" method. This method seems to have some efficiency towards a biological contamination such as a contamination with spores of *Bacillus globigii* [3].

These so-called "L-Gels" are formulated from oxidizing acid solutions to which are added organic solvents and a silica filler. The gels are then sprayed on the surfaces to be treated and then recovered by suction after drying. Among the critical points of this method, the presence of powerful oxidizing agents for which the chemical stability is often highly limited in time appears firstly.

Moreover, in order to avoid runoffs, in particular when the gel (i.e. the gel of document [2] or "L-Gel" is applied on walls or ceilings, the latter is applied as very thin films with a thickness not exceeding, in document [2], 125 μm. The result of this is a powdery dry waste which may cause, if the efficiency of the treatment is not total, dissemination of the biotoxic and chemical species, such as oxidizing compounds, into the atmosphere.

The performances of the method, determined with respect to a contamination by spores of anthrax as an aerosol ($10^7$ and $10^8$ spores per sample of $0.16 \text{ m}^2$), show that it does not allow a reduction in the contamination of more than 4 decades [3].

Moreover, within the scope of nuclear decontamination, gelled formulations which give the possibility of getting rid of the problems related to the powdery nature of the drying waste, of increasing the efficiency of the method applying a gel, have been the subject of documents [4] and [5].

These documents describe inorganic colloidal gels, so-called "vacuumable gels," specifically formulated so as to be sprayed, and then for drying by being fractured, while trapping and confining the radioactive contamination as non-powdery, vacuumable flakes and which may be directly conditioned and stored.

Document [4] describes a gel consisting of a colloidal solution comprising an inorganic viscosifying agent, generally silica or alumina, an active treatment agent which is for example an inorganic acid or base such as soda or potash, and optionally an oxidizing agent having a normal oxidation-reduction potential $E_0$ of more than 1.4 V in a strong acid medium such as Ce(IV), Co(III), or Ag(II).

Document [5] describes a gel consisting of a colloidal solution comprising an organic viscosifying agent, generally silica or alumina, a surfactant, an inorganic acid or base, optionally an oxidizing agent having a normal oxidation-reduction potential $E_0$ of more than 1.4 V in a strong acid medium such as Ce(IV), Co(III), or Ag(II).

These inorganic colloidal gels, because of the different constituents entering their composition have flow properties which allow them to be sprayed on a contaminated surface, and their adhering to this surface, even a vertical surface, without any runoff.

This thus allows prolonged contact between the contaminant and the active decontamination agent, without any alteration of the mechanical properties of the substrate.

Following its spraying, the gel dries, fractures, and produces dry residues, called "flakes," adhering to the substrate and which are subsequently discharged by brushing or suction so as to be directly conditioned.

The decontamination methods which apply these vacuumable gels are therefore decontamination methods via a dry route, not generating any liquid effluents and few dry solid residues. Indeed, these dry solid residues on average only represent a fourth of the mass of initially sprayed gel. Further, these methods limit the exposure time of the operators to the radioactive contamination, because of their easy application by spraying and then suction of the dry residues, and because the presence of the operator is not required during the drying of the gel.

The gels described in documents [4] and [5] are however specifically intended for radioactive decontamination of surfaces notably within the scope of dismantlement of nuclear installations and are by no means adapted or able to be adapted to biological decontamination of surfaces.

Documents FR-A1-2962046 and WO-A1-2012/001046 [1] relate to a "vacuumable" biological decontamination gel and to a method for biologically decontaminating surfaces by using this gel.

This gel is formed by a colloidal solution comprising at least one inorganic viscosifying agent, at least one biological decontamination agent, at least one super-absorbent polymer, and at least one surfactant.

The super-absorbent polymer, such as poly(sodium acrylate), allows improvement in the efficiency of the gel on the porous materials, for example the mortars.

However, this gel and notably the gels described in the examples of this document which comprise alumina, soda, a surfactant and a super-absorbent polymer which is a poly (sodium acrylate), is not sufficiently efficient with view to marketing in the field of NRBC decontamination which requires biological decontamination by at least 6 log, and more exactly comprised between 6 and 8 log.

The super-absorbent polymer such as poly(sodium acrylate), allows improvement in the efficiency of the gel on porous materials, for example mortars.

However, it was shown that the gel of this document has a very short shelf life, for example of a few weeks.

This reduced shelf life is particularly a nuisance when the gel is used for NRBC decontamination. Indeed for such a use, the gel has to be able to be stored for a period of several months, which may even range up to 3 years, and has to be able to be directly available in the case of a post-event intervention.

Therefore considering the foregoing, there exists a need for a biological decontamination gel in which the efficiency of the active biological decontamination agent is improved, in other words for which the biocidal activity is reinforced, as compared with the decontamination gels of the prior art, and for which the stability over time and the shelf life are increased notably as compared with the gel described in document [1].

There notably exists a need for a biological decontamination gel for which the shelf life is sufficiently long so that it allows its use for NRBC decontamination and for which the properties remain intact even after storage for a long period so that the gel is immediately available in the case of "post-event" intervention.

These improvements in terms of efficiency of the active agent, of stability and shelf life, must be obtained without affecting the other physicochemical properties of the gel such as its flow properties or other properties. In particular, the gel should have all the properties of a vacuumable gel with all the advantages related to the application of such a gel in a decontamination method, which have already been discussed above.

This biological decontamination gel should produce non-powdered, dry wastes, easy to remove without dissemination of the biological contaminants, allow treatment with the same efficiency of a large variety of surfaces regardless of their shape, their geometry, their size and their nature.

Further, this gel, considering its final use, should not produce any chemical, mechanical or physical alteration of the treated surfaces.

The goal of the present invention is to provide a biological decontamination gel which inter alia meets the needs and requirements listed above.

The goal of the present invention is further to provide a decontamination gel which does not have the drawbacks, defects, limitations and disadvantages of the biological decontamination gels of the prior art and which solves the problems of the biological decontamination gels of the prior art, notably of the gel object of document [1].

DISCUSSION OF THE INVENTION

This goal, and further other ones are achieved according to the invention with a biological decontamination gel, consisting of a colloidal solution comprising, preferably consisting of:
  5% to 30% by mass, preferably 5% to 25% by mass, still preferably 8% to 20% by mass based on the mass of the gel, of at least one inorganic viscosifying agent;
  an active biological decontamination agent consisting of the combination of a mineral base selected from hydroxides of alkaline metals, hydroxides of earth alkaline metals, and mixtures thereof, and of an oxidizing agent stable in a basic medium selected from permanganates, persulfates, ozone, hypochlorites, and mixtures thereof; the mineral base being present in an amount from 0.05 to 10 mol/L of gel, preferably in an amount from 0.1 to 5 mol/L of gel, and the oxidizing agent stable in a basic medium being present in an amount from 0.05 to 5 mol/L of gel, preferably from 0.1 to 2 mol/L of gel;
  optionally 0.1% to 2% by mass based on the mass of the gel, of at least one surfactant;
  and the balance (remainder) of solvent;
  and the gel not containing any super-absorbent polymer.

By "balance of solvent," is meant that the solvent is always present in the colloidal solution and that the amount of solvent is an amount such that, when it is added to the amounts of the components of the colloidal solution other than the solvent (whether these components are mandatory components or optionally mentioned above, or further other mentioned optional additional components, such as pigments, or not mentioned), the total amount of all the components of the colloidal solution is 100% by mass.

The gels according to the invention have never been described in the prior art.

The gel according to the invention, according to a first fundamental feature, is first of all defined by the fact that it contains an active biological decontamination agent consisting of a specific combination, i.e. the combination of a specific mineral base selected from hydroxides of alkaline metals, hydroxides of earth alkaline metals, and mixtures thereof, and of a specific biocidal oxidizing agent which is an oxidizing agent stable in a basic medium selected from permanganates, persulfates, ozone, hypochlorites and mixtures thereof.

Such an active biological decontamination agent consisting of such a specific combination, is neither described nor suggested in the prior art.

The gel according to the invention is then defined by the fact that it does not contain any super-absorbent polymer.

A fortiori, a biological decontamination gel comprises a specific active biological decontamination agent consisting of said combination of a specific mineral base and of a specific oxidizing agent stable in a basic medium is neither described nor suggested in the prior art.

The gel according to the invention which contains a specific active biological decontamination agent consisting of a combination of a specific mineral base such as a hydroxide of an alkaline metal, like soda, or a hydroxide of an earth alkaline metal, and of a specific oxidizing agent such as a hypochlorite, like sodium hypochlorite, surprisingly has a biocidal activity notably reinforced as compared with gels, such as those of document [1] containing an active biological decontamination agent only consisting of a mineral base such as soda.

It may be stated that the combination of a specific mineral base such as an alkaline hydroxide, such as soda, or an earth alkaline metal hydroxide and of a specific oxidizing agent such as a hypochlorite, like sodium hypochlorite which itself also has a biocidal activity is a real synergistic combination, as explained below.

Indeed, the active biological decontamination agent of the gel according to the invention actually comprises two active biological decontamination compounds, two biocidal compounds, i.e. a first active biocidal compound which is a mineral base such as soda and a second active biocidal compound which is an oxidizing agent such as bleach (sodium hypochlorite) ("Javel"). It is this combination of two active compounds which makes the gel even more efficient.

The oxidizing agent such as bleach (sodium hypochlorite) ("Javel") is not only a simple oxidizing species; it is also an excellent biocide.

Even more surprisingly, the gel according to the invention which therefore has an increased biological activity is however also stable, and has increased stability over time.

Indeed, the inventors showed that poor stability over time of the biological decontamination gel of document [1] was due to the super-absorbent polymer since this super-absorbent polymer modifies the rheology of the gel upon its storage, which makes it unsuitable for spraying and for applying on a vertical surface because of poor adhesion.

The inventors further showed that the use of oxidizing agents in the presence of super-absorbent polymers further considerably reduce the stability over time of the biological decontamination gel of document [1], to a period of less than a few days (see the examples).

The absence of a super-absorbent polymer in the gel according to the invention therefore considerably improves the stability over time.

The gel according to the invention is therefore a considerable improvement in the formulation of biological decontamination gels of the prior art and notably of the gel object of document [1], both from the point of view of its biocidal efficiency and of its stability over time.

It may be stated that in the biological decontamination gel according to the invention, the efficiency of the decontamination active is improved on the one hand, and the stability of the gel is increased on the other hand by doing without the addition of a super-absorbent polymer.

More exactly, quite surprisingly, and unlike what may have been expected considering the results obtained with the biological decontamination gel of document [1], the gel according to the invention has biocidal activity for example greater by 2 to 3 orders of magnitude relatively to the gel of the document [1], without however being altered over time, i.e. over a period for example of: see the examples.

Preferably, the mineral base is selected from sodium hydroxide, potassium hydroxide, and mixtures thereof, and the oxidizing agent stable in a basic medium is selected from hypochlorites, and mixtures thereof.

A more preferred active biological decontamination agent consists of the combination of soda and of sodium hypochlorite.

In this case, soda is present in an amount from 0.05 to 10 mol/L of gel, preferably 0.5 to 5 mol/L of gel, and sodium hypochlorite is present in an amount from 0.05 to 5 mol/L of gel, preferably from 0.1 to 1.5 mol/L of gel.

Indeed, by adding sodium hypochlorite (bleach concentrate, "Javel" concentrate) it is possible to reinforce the biocidal aggressivity of the gel according to the invention and therefore to increase the biological decontamination factor thereof relatively to a gel only containing soda (FIG. 2) without fundamentally modifying the physicochemical properties or the flow properties thereof. Soda, as for it is also a good biocide. Further it is an excellent stabilizer for sodium hypochlorite, and it guarantees good preservation of the hypochlorite ion content while ensuring a biocidal function.

As a summary, the gels according to the invention therefore meet the whole of the needs mentioned above, they do not have the drawbacks, defects, limitations and disadvantages of the biological decontamination gels of the prior art, such as those described in the documents mentioned above.

The gels according to the invention thus solve the problems exhibited by the biological decontamination gels of the prior art without having the drawbacks thereof, but while retaining all the known advantageous properties of these gels, notably their "vacuumable" ("aspirable", "suckable") nature.

The gel according to the invention is a colloidal solution, which means that the gel according to the invention contains inorganic, mineral solid particles of a viscosifying agent for which the elementary primary particles have a size generally from 2 to 200 nm.

Because of the application of a viscosifying agent generally and exclusively inorganic agent, without any organic viscosifying agent, the content of organic materials of the gel according to the invention is generally less than 4% by mass, preferably less than 2% by mass, which is further another advantage of the gels according to the invention.

These inorganic, mineral, solid particles play the role of a viscosifying agent in order to allow gelling of the solution, for example the aqueous solution and thus adhesion to the surfaces to be treated, decontaminated, regardless of their geometry, their shape, their size and regardless of where the contaminants to be removed are found.

Advantageously, the inorganic viscosifying agent may be selected from metal oxides such as aluminas, metalloid oxides except for silica, hydroxides of metals, hydroxides of metalloids, oxyhydroxides of metals, oxyhydroxides of metalloids, aluminosilicates, clays such as smectite, and mixtures thereof; these viscosifying agents are stable in a basic medium.

In particular, the inorganic viscosifying agent may be selected from aluminas ($Al_2O_3$).

The inorganic viscosifying agent may only comprise a single alumina or a mixture thereof, i.e. a mixture of two different aluminas, or more ($Al_2O_3/Al_2O_3$ mixture).

The alumina may be selected from calcined aluminas, milled calcined aluminas, and mixtures thereof.

As an example, mention may be made of the product sold by EVONIK INDUSTRIES under the trade name of "Aeroxide Alu C" which is pyrogenated fine alumina and which has a BET specific surface area of 100 $m^2/g$.

Advantageously, according to the invention, the viscosifying agent consists of one or several alumina(s). This or these alumina(s) generally represent from 5% to 30% by mass based on the mass of the gel.

In this case, the alumina(s) is(are) preferably at a concentration from 8% to 17% by mass based on the total mass of the gel (in order to ensure drying of the gel at a temperature comprised between 20° C. and 50° C. and at a relative humidity comprised between 20% and 60% on average for 30 minutes to 5 hours).

The nature of the mineral viscosifying agent, notably when it consists of one or several alumina(s), unexpectedly influences the drying of the gel according to the invention and the grain size of the obtained residue.

Indeed, the dry gel appears as particles with a controlled size, more specifically millimetric solid flakes, for which the size generally ranges from 1 to 10 mm, preferably from 2 to 5 mm notably by means of the aforementioned compositions of the present invention, in particular when the viscosifying agent consists of one or several alumina(s).

Let us specify that the size of the particles generally corresponds to their largest dimension.

The gel according to the invention contains an active biological decontamination agent as defined above.

By biological decontamination agent which may also be described as a biocidal agent, is meant an agent, which, when it is put into contact with a biological species and notably a toxic biological species is able to inactivate or kill the latter.

By biological species, is meant any type of micro-organism such as bacteria, fungi, yeasts, viruses, toxins, spores, notably spores of *Bacillus anthracis*, prions and protozoa.

The biological species which are removed, destroyed, inactivated by the gel according to the invention are essentially biotoxic species such as pathogenic spores such as for example the spores of *Bacillus anthracis*, bacteria such as for example the *Yersinia pestis* bacteria, toxins such as for example botulinic toxin or ricin, and viruses such as for example viruses of vaccinia or viruses of hemorrhagic fevers (for example of the Ebola type).

The active biological decontamination agent is used at the concentrations mentioned above, in order to guarantee a power of removal of biological, notably biotoxic species, compatible with the drying time of the gel and for ensuring for example drying of the gel at a temperature comprised between 20° C. and 50° C. and at a relative humidity comprised between 20% and 60% on average for 30 minutes to 5 hours.

It should be noted that as the gel of the invention is a basic gel, in addition to the decontamination action it has a degreasing action.

In order to attain total efficiency, including under the most unfavorable weather conditions towards the drying time of the gel, the gel according to the invention may have a large range of concentrations of basic biological decontamination agent(s).

Indeed, the increase in the concentration of basic biological decontamination agent like NaOH or KOH, generally playing the role of a biocidal agent, gives the possibility of considerably increasing the destruction rates of biological species, such as for example the spores of *Bacillus thuringiensis* (similar to the spores of *Bacillus anthracis*).

The mineral base is used at the concentration defined above for ensuring drying of the gel at a temperature comprised between 20° C. and 50° C. and at a relative humidity comprised between 20% and 60% on average for 30 minutes to 5 hours.

In the case of the treatment of a cement matrix, the basic pH of the gel, which is induced for example by the use of soda or potash, gives the possibility of avoiding acid-basic reactions, between the material to be decontaminated and the gel, which are detrimental to the integrity of the material but also to that of the gel on the surface and therefore to the efficiency of the method.

The hygroscopicity of the sodium hydroxide or potassium hydroxide is also a considerable asset for slowing down the gel drying phenomenon. The contact time between the gel according to the invention, for example containing a biocidal solution, and the biological contamination, is then considerably increased.

Indeed, the competition between the process for evaporating the aqueous phase and that for taking up water from the sodium hydroxide or potassium hydroxide crystals favorably modifies the drying kinetics of the gel.

According to the invention, the gel in accordance with the invention does not contain, unlike the gel described in document [1], any super-absorbent polymer, in other words the gel according to the invention is free of any super-absorbent polymer.

By "super-absorbent polymer" also called "SAP", is generally meant a polymer capable, in the dry condition, of spontaneously absorbing at least 10 times or preferably at least 20 times its aqueous liquid weight, in particular water and notably distilled water. Such super-absorbent polymers were described in detail in the already mentioned document [1].

The gel may also contain, optionally, a surfactant or a mixture of surfactants, preferably selected from non-ionic surfactants such as sequenced, block, copolymers like block copolymers of ethylene oxide and of propylene oxide, and ethoxylated fatty acids; and mixtures thereof.

For this type of gel, the surfactants are preferably block copolymers marketed by BASF under the name of "Pluronic®". For example Pluronic® PE6200 may be used.

The Pluronics® are block copolymers of ethylene oxide and of propylene oxide.

These surfactants influence the rheological (flow) properties of the gel, notably the thixotropy of the product and the recovery time, in order to make it sprayable both on floors, walls or ceilings while avoiding the occurrence of runoff.

The surfactants moreover give the possibility of controlling the adhesion of the dry waste and of controlling the size of the flakes of dry residue in order to guarantee the non-powdery nature of the waste. These surfactants finally give the possibility of controlling the bleeding phenomenon of the gel over time and thus therefore improve its capability of being sprayed after storage.

The solvent according to the invention is generally selected from water, organic solvents, and mixtures thereof.

A preferred solvent is water, and in this case, the solvent consists of water, comprises 100% of water.

Advantageously, the gel according to the invention may further comprise at least one mineral pigment such as iron oxide.

Generally, the colloidal solution may comprise from 0.01% to 10% by mass, preferably from 0.1% to 5% by mass based on the mass of the gel, of said at least one mineral pigment.

There is no limitation as to the mineral pigment which is incorporated into the decontamination gel according to the invention.

Generally, the mineral pigment is selected from mineral pigments which are stable in the gel, notably considering the active decontamination agent which the gel contains.

By stable pigment, is generally meant that the pigment does not exhibit any stable change of its color over time, during storage of the gel for a minimum period of 6 months.

There is no limitation as to the color of this pigment, which is generally the color which it will impart to the gel. This pigment may be of a black, red, blue, green, yellow, orange, violet, brown color, etc., and even white.

Generally, the gel therefore has a color identical with the color of the pigment which it contains. It is however possible that the gel has a color which differs from the color of the pigment which it contains, for example in the case when the pigment reacts with the decontamination active agent, but this is not desired.

The pigment, notably when it is white, is generally different from the inorganic viscosifying agent.

Advantageously, the mineral pigment is selected so that it gives to the gel (i.e. to the gel in the wet state as defined above, before drying) a color different from the color of a surface to be decontaminated onto which the gel is applied.

Advantageously, the mineral pigment is a micronized pigment, and the average size of the particles of the mineral pigment may be from 0.05 to 5 µm, preferably from 0.1 to 1 µm.

By the fact that the pigment is micronized, it is possible to avoid that it modifies the flow properties and the capability of spraying the gel ("sprayability") since the pigment then has the same micrometric size which is generally that of the inorganic viscosifying agent, such as alumina aggregates.

Advantageously, the mineral pigment is selected from oxides of metal (metals) and/or of metalloid(s), hydroxides of metal (metals) and/or of metalloid(s), oxyhydroxides of metal (metals) and/or of metalloid(s), ferrocyanides and ferricyanides of metal (metals), aluminates of metal (metals), and mixtures thereof.

Preferably, the mineral pigment is selected from iron oxides, preferably micronized, and mixtures thereof.

The iron oxides may have different colors; they may for example be yellow, red, violet, orange, brown or black.

Indeed, the iron oxide pigments are recognized as having a good covering power and great resistance to acids and bases.

For incorporation in a decontamination gel, iron oxides have the best performances in terms of stability and of coloring power. Thus, an iron oxide content of 0.1%, or even 0.01% by mass is sufficient for strongly coloring the gel without modifying the properties thereof.

As this was already indicated above, by the fact that the iron oxide pigment is preferably micronized, it is possible to avoid that it modifies the flow properties and the capability of spraying the gel ("sprayability") since the pigment then has a micrometric size, i.e. a size which is generally that of the inorganic viscosifying agent, such as alumina aggregates.

Micronized iron oxides are available from Rockwood® under the trade name of Ferroxide®.

Mention may be made inter alia of Ferroxide® 212 M which is a micronized red iron oxide with an average particle size of 0.1 µm and Ferroxide® 228 M which is a micronized red iron oxide with an average particle size of 0.5 µm.

In addition to and/or instead of iron oxides, other colored oxides or hydroxides of metals or metalloids may be incorporated into the gel according to the invention, depending on the pH of the gel, mention may notably be made of vanadium oxide ($V_2O_5$) which is orange, manganese oxide ($MnO_2$) which is black, cobalt oxide which is blue or green, and rare earth oxides. However, iron oxides are preferred for the reasons specified above.

From among oxyhydroxides, mention may be made of goethites, i.e. iron 'oxyhydroxide FeOOH which is highly colored.

As an example of a metal ferrocyanide, mention may be made of Prussian blue, i.e. ferric ferrocyanide, or as an example of aluminate, mention may be made of cobalt blue, i.e. cobalt aluminate.

The incorporation into the gel according to the invention of a mineral pigment gives the possibility of better viewing the wet gel and then the dry residues regardless of the substrate on which the gel is applied.

Surprisingly, it was shown that the specific coloring substance which may be incorporated into the gel according to the invention which is a mineral pigment does not affect the decontaminating and physicochemical properties of the decontamination gel according to the invention which is, like gels without any inorganic pigments, sprayable, vacuumable after drying and which may be used in many situations on a large range of biological contaminants and substrates.

In other words, it was shown that among all the coloring agents and pigments which might have been used for giving color to the biological decontamination gels according to the invention which may be sprayed and vacuumed, only mineral pigments, more particularly pigments based on oxides of metal (metals) and/or of metalloid(s), of hydroxides of metal (metals) and/or of metalloid(s), oxyhydroxides of metal (metals) and/or of metalloid(s), of ferrocyanides and ferricyanides of metal, of aluminates of metal (metals), and mixtures thereof; and still more particularly the pigments based on micronized iron oxides, being compatible with the formulation of the oxidizing alkaline decontamination gel according to the invention, i.e. by no means affected the required properties of the gels according to the invention and the advantages which ensue therefrom.

Surprisingly, only mineral pigments, more particularly pigments based on oxides, hydroxides, oxyhydroxides, ferrocyanides, ferricyanides, and aluminates, still more particularly the pigments based on micronized iron oxides, provide good coloring power and good preservation of the coloration over time without however notably modifying the properties (see above) of the oxidizing alkaline gel formulated according to the invention.

The optional addition of mineral pigments to the gel according to the invention gives the possibility by many aspects, of facilitating and improving its application, notably as regards their use in disaster-stricken areas, in an emergency situation in confined media or with reduced visibility, in particular for operators in NRBC coveralls.

The optional presence of mineral pigments in the gel according to the invention not only ensures better viewing of the areas covered by the humid gel after spraying but also better viewing of the dry flakes on the decontaminated support.

Another additional advantage of the optional incorporation of a pigment in the gel according to the invention is that it gives the possibility of easily distinguishing the dry areas, i.e. the areas covered by the dry gel flakes, from the still wet gel areas.

This is possible by discoloration of the gel during drying if, of course, the pigment is not a white pigment.

It is thus possible to visually make sure, easily and certainly that the action of the gel is completed and that the duration during which it remained on the substrate was sufficient for allowing complete drying of the gel, even when this duration is random and varies depending on the weather conditions, i.e. notably on the temperature, relative humidity, and the ventilation.

The invention further relates to a method for biologically decontaminating a surface of a solid substrate contaminated with at least one biological species found on said surface, in which at least one cycle is carried out comprising the following successive steps:

a) the gel according to the invention as described above is applied on said surface;

b) the gel is maintained on the surface at least for a sufficient time (duration) so that the gel destroys and/or inactivates and/or absorbs the biological species, and so that the gel dries and forms a dry and non-powdered solid residue possibly containing said biological species;

c) the dry and solid residue possibly containing said biological species is removed.

Generally, the solid residues do not contain any living biological species.

The destroyed "killed" biological contamination is recovered by the dry gel flakes.

Advantageously, the substrate is made of at least one material selected from metals and alloys such as stainless steel; painted steel; polymers such as plastic materials or rubbers like poly(vinyl chloride)s or PVC, polypropylenes or PP, polyethylenes or PE notably high density polyethylenes or HDPE, poly(methyl methacrylate)s or PMMA, poly (vinylidene fluoride)s or PVDF, polycarbonates or PC; glasses; cements; mortars and concretes; plasters; bricks; natural or artificial stone; ceramics.

Advantageously, the biological species is selected from among the toxic biological species already listed above.

Advantageously, the gel is applied on the surface to be decontaminated in an amount from 100 g to 2,000 g of gel per $m^2$ of surface, preferably from 500 to 1,500 g of gel per $m^2$ of surface, still preferably from 600 to 1,000 g of gel per $m^2$ of surface, which generally corresponds to a gel thickness deposited on the surface comprised between 0.5 mm and 2 mm.

Advantageously, the gel is applied on the solid surface by spraying, with a brush, or with a trowel.

Advantageously (during step b)), drying is carried out at a temperature from 1° C. to 50° C., preferably from 15° C. to 25° C., and under relative humidity from 20% to 80%, preferably from 20% to 70%.

Advantageously, the gel is maintained on the surface for a period from 2 to 72 hours, preferably from 2 to 48 hours, still preferably from 3 to 24 hours.

Advantageously, the dry and solid residue appears as particles, for example flakes, with a size from 1 to 10 mm, preferably from 2 to 5 mm.

Advantageously, the dry and solid residue is removed from the solid surface by brushing and/or suction.

Advantageously, the cycle described above may be repeated for example from 1 to 10 times by using the same gel during all the cycles or by using different gels during one or several cycles.

Advantageously, during step b), the gel, before total drying, is rewetted with a solution of a biological decontamination agent, preferably with the solution of the biological active agent of the gel applied during step a) in the solvent of this gel.

During step b), the gel may before total drying be rewetted with the biocidal solution contained in the biological decontamination gel already described above, which then generally avoids repetition of the application of the gel on the surface and causes savings in reagent and a limited amount of waste. This re-wetting operation may be repeated.

As a summary, the method and the gel according to the invention have, inter alia, the following advantageous properties:
application of the gel by spraying,
adherence to the walls,
obtaining the maximum decontamination efficiency at the end of the drying phase of the gel.

Generally, it is ensured that the drying time is greater than or equal to the duration required for inactivation.

treatment via a dry route of a very wide range of materials, the absence of any mechanical or physical alteration of the materials at the end of the treatment, the application of the method under variable weather conditions, reduction in the volume of waste, facility for recovering the dry waste, low exposure of the operators to the contamination.

Other features and advantages of the invention will become better apparent upon reading the detailed description which follows, this description being made as an illustration and not as a limitation, in connection with the appended drawings.

On this graph for each support is plotted the number of spores initially deposited on the support (initial contamination) (left bar) and in the flakes (non-milled or milled in the latter case) (right bar).

Figure 9:
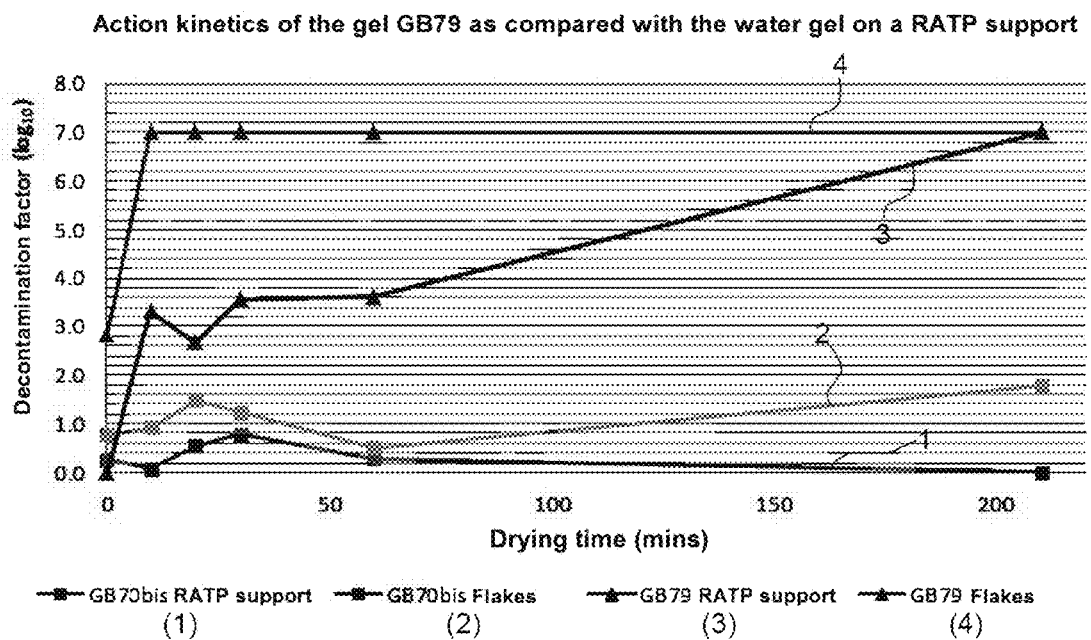

FIG. 9 is a graph which shows the action kinetics of the inactive gel GB70bis with water and of the gel GB79 according to the invention on spores of *Bacillus thuringiensis*. The gels are applied on ceramic tiles provided by RATP.

In abscissas is plotted the drying time (in min.) and in ordinates is plotted the decontamination factor ($\log_{10}$).

Curve 1 relates to the gel GB70bis, curve 2 relates to the flakes of the gel GB70bis, curve 3 relates to the gel GB79, and curve 4 relates to the flakes of the gel GB79.

Figure 10:
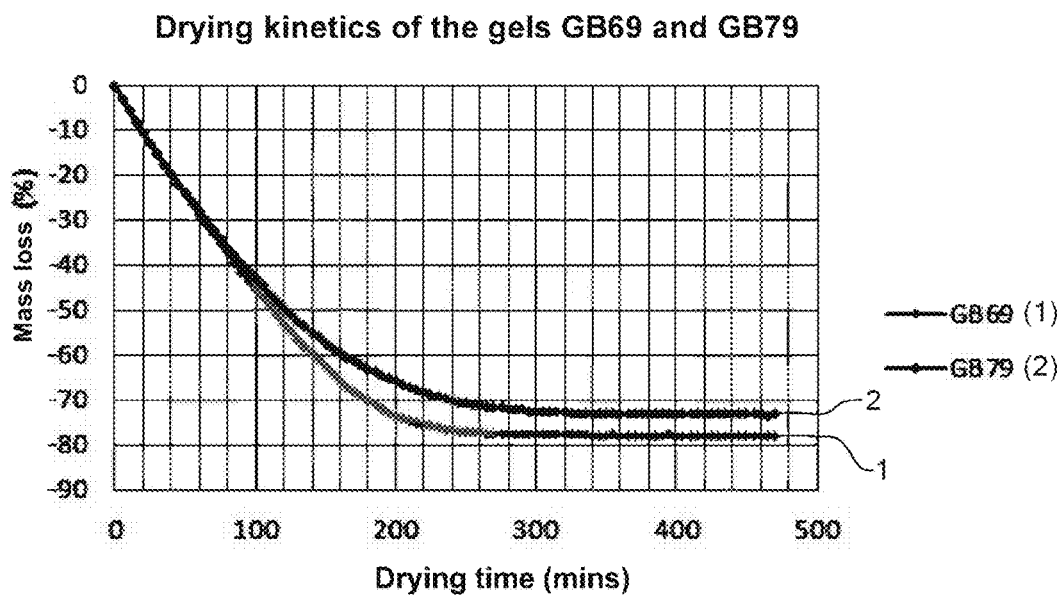

FIG. 10 is a graph which shows the drying kinetics, under a controlled atmosphere (Temperature: 25° C.; relative humidity: 50%; aperture of the door of the scale: 3 cm; gel thickness: 0.5 mm), of the gel GB69 and of the gel GB 79 according to the invention.

In abscissas is plotted the drying time (in min.), and in ordinates is plotted the mass loss (in %).

Curve 1 represents the drying kinetics of the gel GB69 and curve 2 represents the drying kinetics of the gel GB79.

Figure 11:
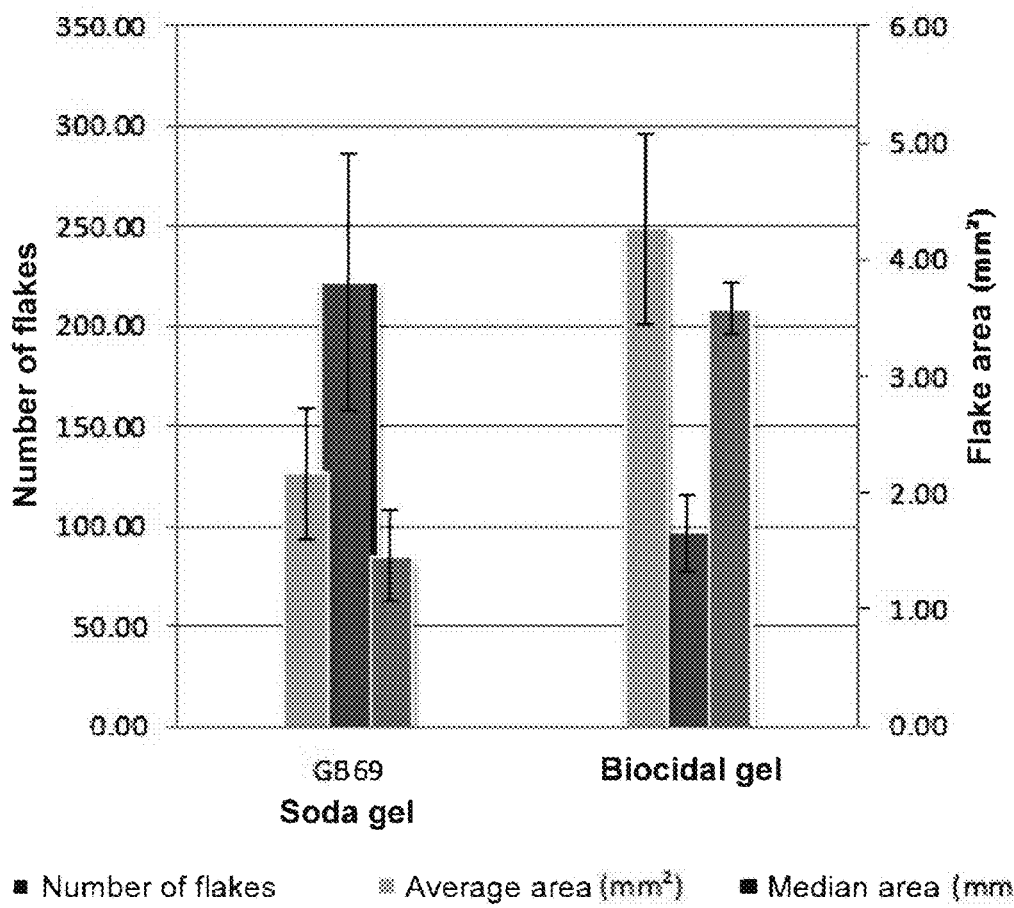

FIG. 11 is a graph which compares fracturation under a controlled atmosphere (Temperature: 25° C.; relative humidity: 50%; aperture of the door of the scales: 3 cm; gel thickness: 0.5 mm) of the gel with soda GB69 and of the biocidal gel with bleach and with soda GB79 according to the invention (on the right).

The left scale indicates the number of flakes, and the right scale indicates the area of the flakes (in $mm^2$).

For each gel is plotted the average area of the flakes (in $mm^2$) (left bar), the number of flakes (middle bar), and the mean area (in $mm^2$) (right bar).

Figure 12:
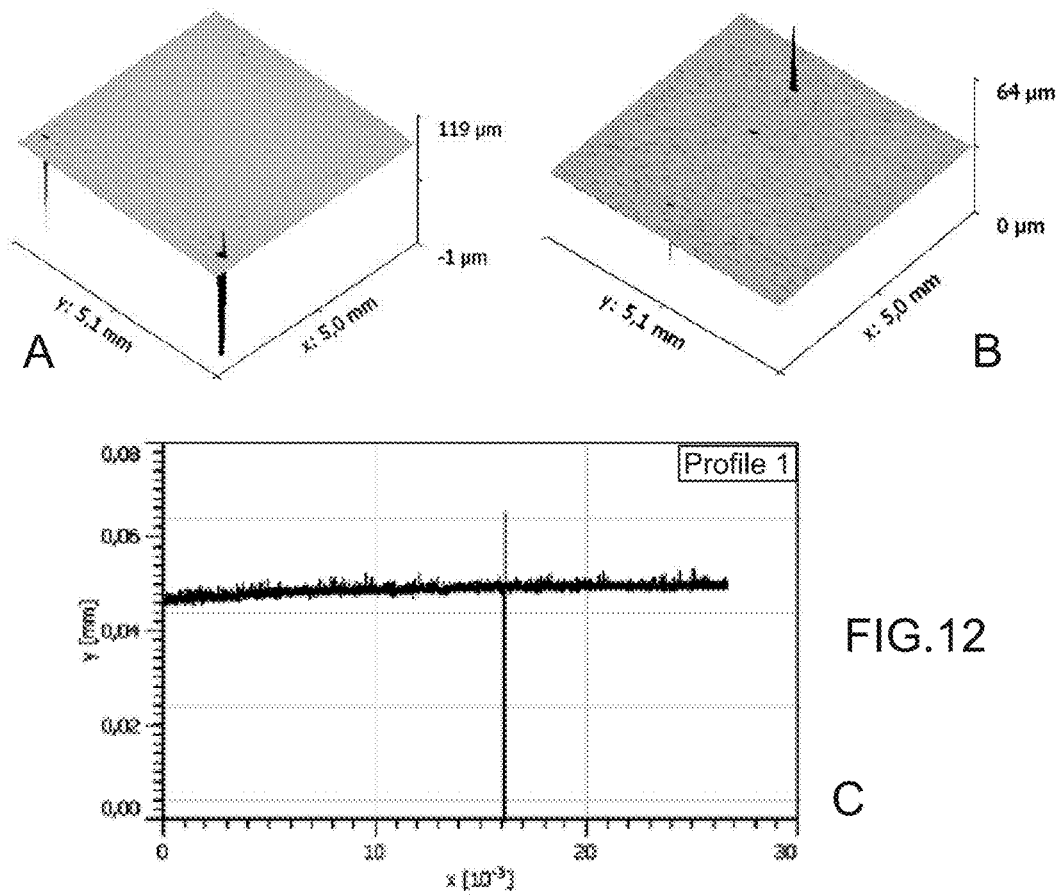

FIG. 12 represents the 3D mapping and the profile obtained with the optical profilometer along a stainless steel support, one portion of which has been treated with the gel GB79 according to the invention and one portion of which has not been treated with this gel, and has remained blank.

FIG. 12A represents the 3D mapping of the portion of the support which has been treated with the gel according to the invention and FIG. 12B represents the 3D mapping of the portion of the support which has not been treated with this gel.

In FIG. 12C, the left portion of the profile before the separation is the profile of the portion of the support treated with the gel according to the invention, and the right portion of the profile after the separation is the profile of the portion of the support which has not been treated with the gel according to the invention.

Figure 13:
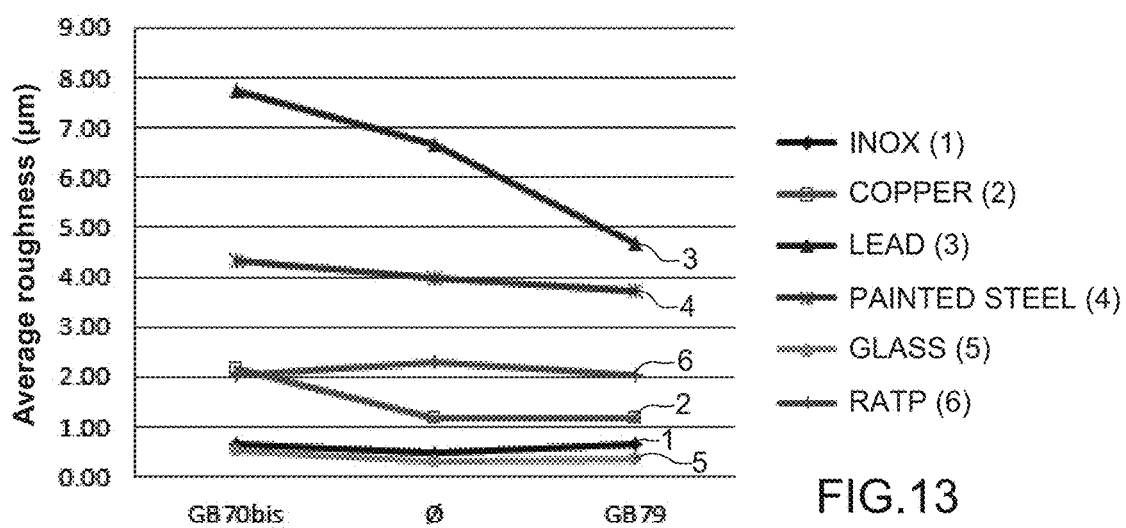

FIG. 13 is a graph which gives the average roughnesses (in µm) measured with the optical profilometer of the surface of supports in different mineral materials, i.e. made of stainless steel (curve 1 "INOX"), copper (curve 2), lead (curve 3), painted steel (curve 4), glass (curve 5), and made of ceramic (ceramic tile provided by the RATP: curve 6 "RATP").

Each of these surfaces includes three areas for which measurements were carried out: a first area is treated with the inactive gel with water GB70bis, a second area is not treated (illustrated by Ø on the graph), and a third area is treated with the active gel GB79 according to the invention.

Figure 14:
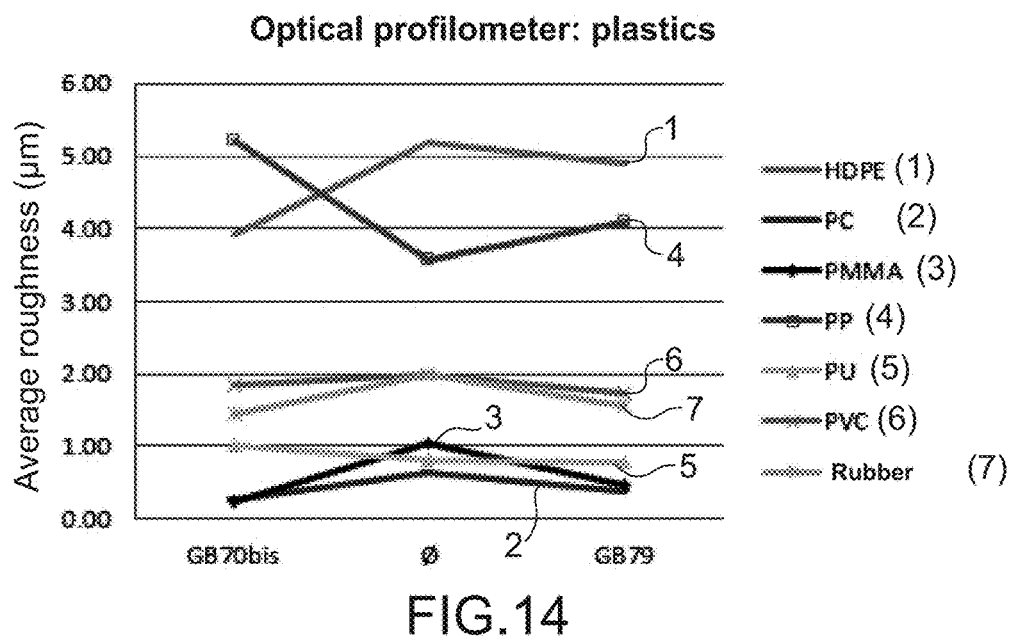

FIG. 14 is a graph which gives the average roughnesses (in µm) measured with the optical profilometer of the surface of supports made of various plastic organic materials, i.e. made of high density polyethylene (HDPE) (curve 1), made of polycarbonate (PC) (curve 2), made of poly(methyl methacrylate) (PMMA) (curve 3), made of polypropylene (PP) (curve 4), made of polyurethane (PU) (curve 5), made of poly(vinyl chloride) (PVC) (curve 6), and made of rubber (curve 7).

Each of these surfaces includes three areas for each of which measurements were carried out: a first area is treated with the inactive gel with water GB70bis, a second area is not treated (illustrated by Ø on the graph), and a third area is treated with the active gel GB79 according to the invention.

Figure 15:
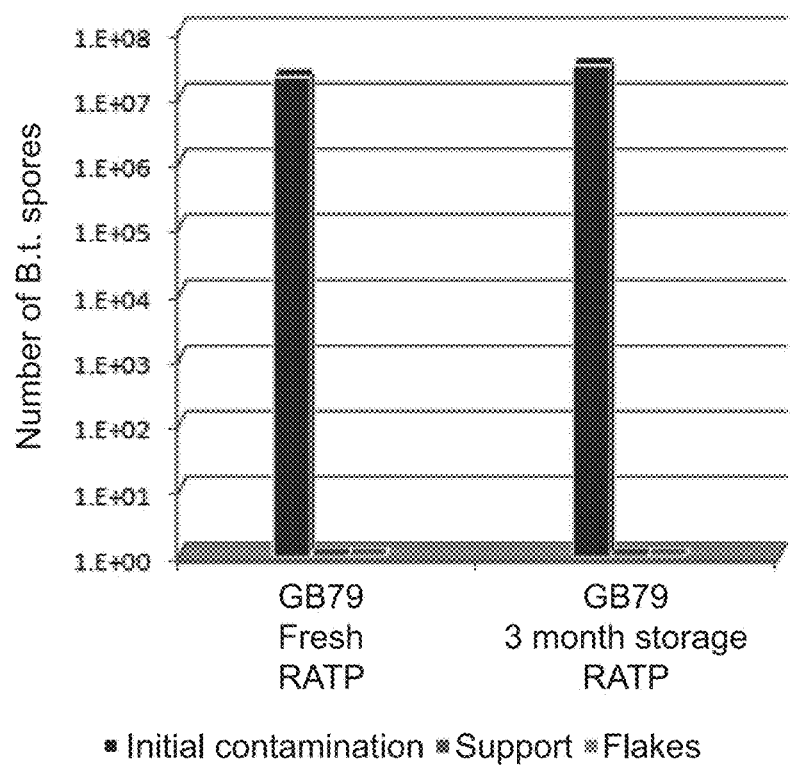

FIG. 15 is a graph which shows the biocidal efficiency of a fresh gel GB79 according to the invention (3 left bars) and after 3 months of storage (3 right bars) on supports which are ceramic tiles provided by the RATP, contaminated with spores of *Bacillus thuringiensis*.

The left scale indicates the number of counted spores of *Bacillus thuringiensis*.

For each gel, is plotted from left to right the number of spores initially deposited (initial contamination), detected on the support, and in the flakes.

Figure 16:
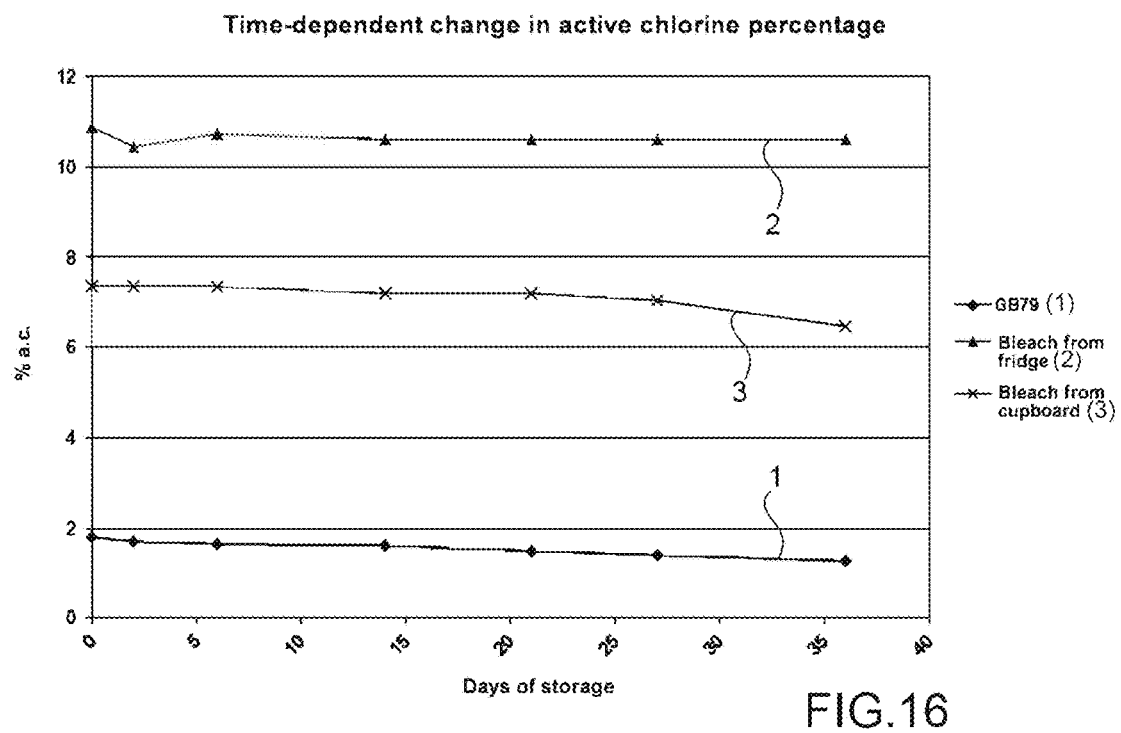

FIG. 16 is a graph which shows the time-dependent change in the active chlorine percentage in the gel GB79 according to the invention (♦) (curve 1), in bleach stored in the refrigerator (▲) (curve 2), and in bleach stored in the laboratory (x) (curve 3).

In ordinates is plotted the active chlorine % (% a.c.), and in abscissa is plotted the number of days of storage.

Figure 17:
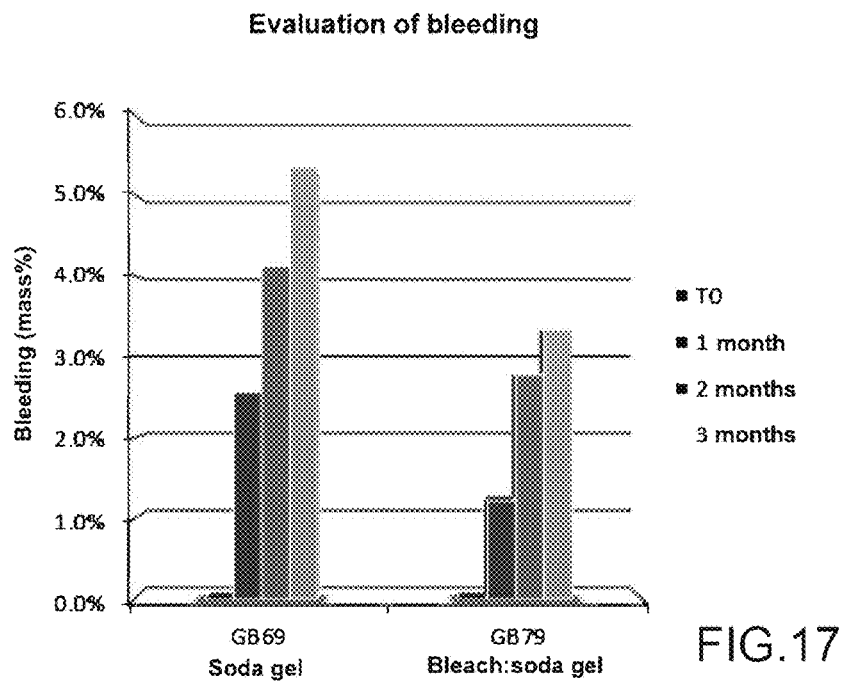

FIG. 17 is a graph which shows bleeding of the gel with soda GB69 (on the left) and of the gel according to the invention GB79 (on the right).

The left scale indicates bleeding (in mass %).

For each gel is plotted the bleeding at T0, (the left most bar) and for storage periods of 1 month, 2 months, and 3 months.

Figures 18, 19:
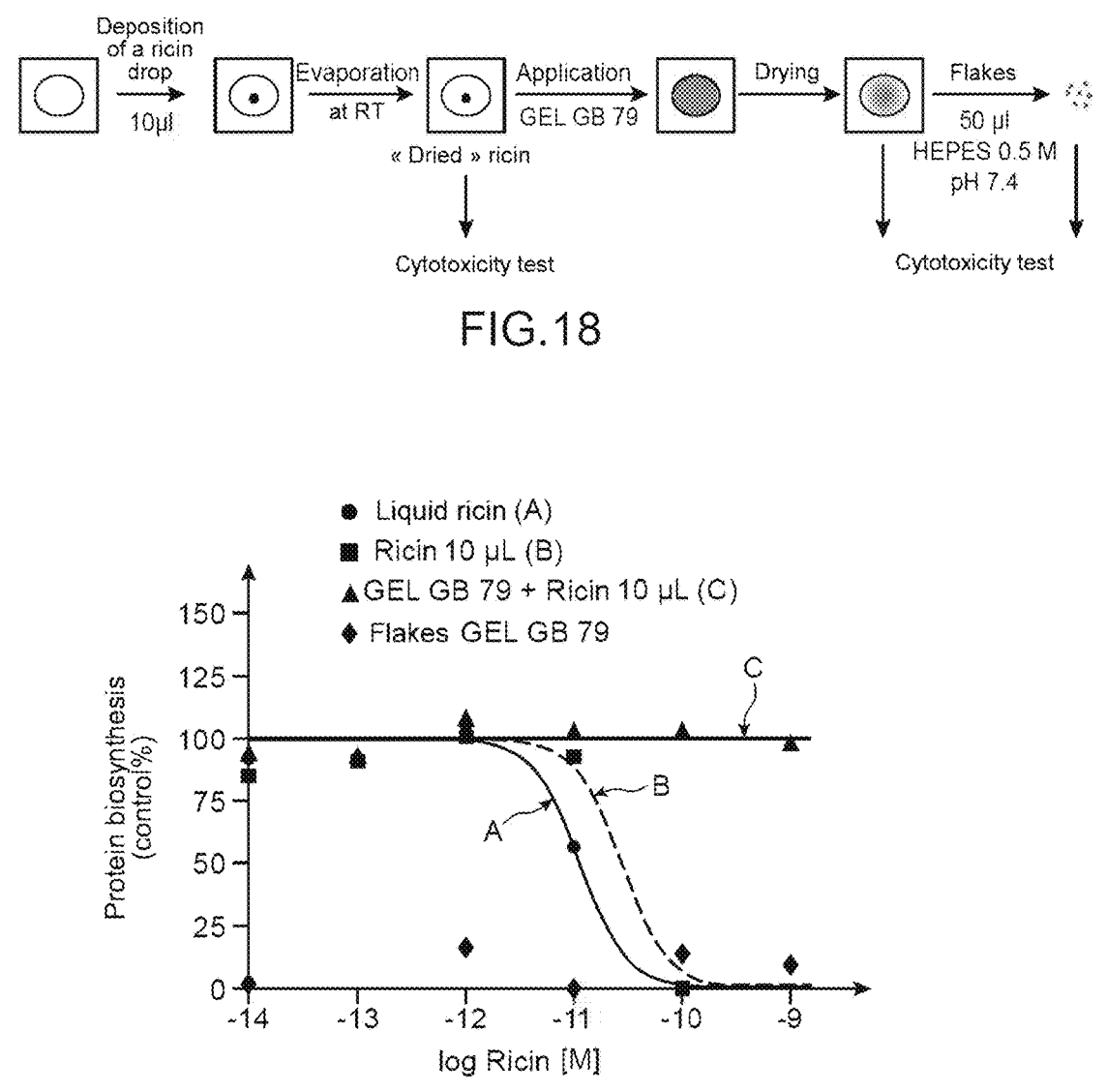

FIG. 18 shows the operating procedure followed for testing the efficiency of the gel according to the invention GB79 on ricin.

FIG. 19 is a graph (cytotoxicity curves) which shows the results of cytotoxicity tests showing the effect of ricin on the cells, and the effect of the gel GB79 according to the invention on ricin. This cytotoxicity is evaluated by measuring the protein biosynthesis by these cells. The greater the cytotoxicity, the lower is the biosynthesis.

The effect on these cells of liquid ricin was tested (curve A, in solid line, points ●), of "dried" ricin after evaporation at room temperature (curve B, in dotted lines, points ■), of ricin after applying on the dried ricin the gel GB79 according to the invention and drying (curve C, in dash lines, points ▲), of ricin present in the dry gel flakes (points ♦).

In ordinates is plotted the protein biosynthesis (in % of the control) and in abscissas is plotted the log Ricin (M).

Figure 20:
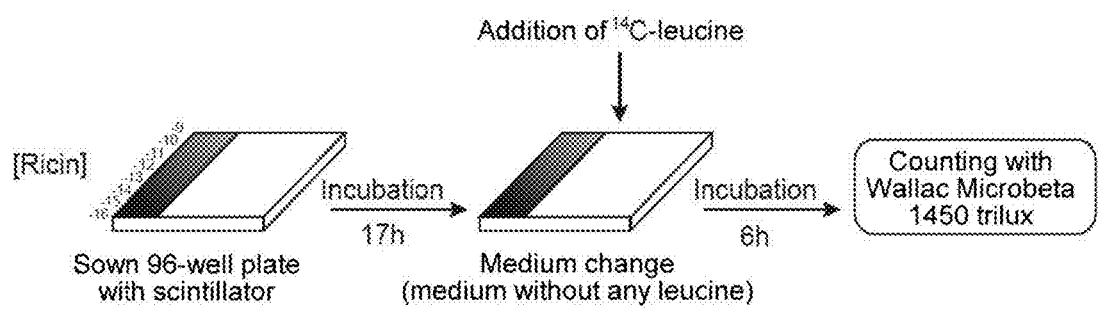

FIG. 20 shows the principle of the cytotoxicity test described in annex 1.

Figure 21:
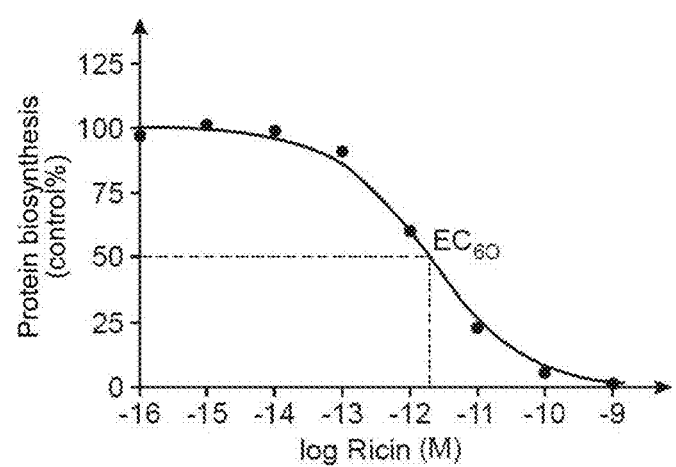

FIG. 21 shows an exemplary cytotoxicity curve.

In ordinates is plotted the protein biosynthesis (in % of the control) and in abscissas is plotted the log Ricin (M).

DETAILED DISCUSSION OF PARTICULAR EMBODIMENTS

The gel according to the invention may be easily prepared at room temperature.

For example, the gel according to the invention may be prepared by adding preferably gradually, the inorganic viscosifying agent(s), for example alumina(s) and/or silica(s), to a solution containing the active biological decontamination agent (formed by the combination of an inorganic base and of an oxidizing agent), possible surfactant(s), and optional pigment(s). This solution may be for example prepared by first of all preparing a solution of the oxidizing agent, for example a solution of sodium hypochlorite in demineralized water, and then by mixing with this solution of oxidizing agent, the mineral base, optional surfactant(s), and optional pigment(s). This mixture may be achieved by mechanical stirring, for example by means of a mechanical stirrer equipped with a three-blade propeller. The speed of rotation is for example of 200 rpm, and the stirring period is for example from 3 to 5 minutes.

The addition of the inorganic viscosifying agent(s) to the solution containing the active biological decontamination mixture, the optional surfactant(s), and the optional pigment(s) may be achieved by simply pouring the viscosifying agent(s) into said solution. During addition of the inorganic viscosifying agent(s), the solution containing the active biological decontamination mixture, the optional surfactant(s), and the optional pigment(s) is generally maintained with mechanical stirring.

This stirring may for example be achieved by means of a mechanical stirrer equipped with a three-blade propeller.

The stirring rate is generally gradually increased as the viscosity of the solution increases, in order to finally attain a stirring rate for example comprised between 400 and 600 revolution/minute, without there being any projections.

After the end of the addition of the mineral viscosifying agent(s), stirring is further continued, for example for 2 to 5 minutes, so as to obtain a perfectly homogenous gel.

It is quite obvious that other procedures for preparing the gels according to the invention may be applied with addition of the components of the gel in an order different from the one mentioned above.

Generally, the gel according to the invention should have a viscosity of less than 200 mPa·s under shearing of 1,000 s$^{-1}$ so as to allow spraying on the surface to be decontaminated, at a distance (for example at a distance from 1 to 5 m) or close (for example at a distance of less than 1 m, preferably from 50 to 80 cm). The time for recovering viscosity should generally be limited to one second and the viscosity under low shearing should be greater than 10 Pa·s in order to not run on the wall.

It should be noted that the optional surfactant of the gel according to the invention favorably influences notably the flow properties of the gel according to the invention. This surfactant notably gives the possibility that the gel according to the invention may be applied by spraying and avoids the risks of spreading or running during the treatment of vertical surfaces and of ceilings. This surfactant also allows limitation of the bleeding phenomenon observed during storage of the gel.

The thereby prepared gel according to the invention is then applied (1) (FIG. 1A) on the solid surface (2) to be decontaminated of a substrate in a solid material (3), in other words on the surface (2) having been exposed to biological contamination (4); this biological contamination (4) may consist in one or several of the biological species already defined above.

Except for possibly the alloys of light-weight metals of the aluminium type, there is no limitation as to the material which forms the surface (2) to be decontaminated, indeed, the gel according to the invention gives the possibility of treating without any damaging, all sorts of materials, even fragile materials.

The gel according to the invention does not generate any alteration, erosion, chemical, mechanical or physical attack of the treated material. The gel according to the invention is therefore by no means detrimental to the integrity of the treated materials and even allows them to be reused. Thus, sensitive hardware such as military equipments are preserved and after their decontamination may be reused, while monuments treated with the gel according to the invention are absolutely not degraded and their visual and structural integrity is preserved.

This material of the substrate (3) may therefore be selected from among, for example, metals or alloys like stainless steel, polymers such as plastic material or rubbers among which mention may be made of PVC, PP, PE notably HDPE, PMMA, PVDF, PC, glasses, cements, mortars and concretes, plasters, bricks, natural or artificial stone, ceramics.

In every case (see Example 4 and FIG. 7), regardless of the material, the decontamination efficiency with the gel according to the invention is total.

The treated surface may be painted or not painted.

Also there is no limitation as to the shape, the geometry and the size of the surface to be decontaminated, the gel according to the invention and the method applying it allow treatment of surfaces of large size, of complex geometries, for example having cavities (recesses), angles, corners.

The gel according to the invention ensures efficient treatment not only of horizontal surfaces such as floors, but also of vertical surfaces such as walls, or of tilted or overhanging surfaces such as ceilings.

As compared with existing biological decontamination methods which apply liquids such as solutions, the decontamination method according to the invention which applies a gel is particularly advantageous for treating materials with a large surface, which are not transportable and implanted outdoors. Indeed, the method according to the invention because of the application of the gel, allows decontamination in situ while avoiding the spreading of chemical solutions in the environment and dispersion of the contaminating species.

The gel according to the invention may be applied on the surface to be treated by all the application methods known to the man skilled in the art.

Conventional methods are spraying for example with a gun or application by means of a brush, or of a trowel.

For applying by spraying the gel according to the invention on the surface to be treated, the colloidal solution may for example be conveyed via a low pressure pump, for example a pump which applies a pressure of less than or equal to 7 bars, i.e. about $7 \cdot 10^5$ Pascals.

The bursting of the gel jet on the surface may for example be obtained by means of a nozzle with a flat jet or with a round jet.

The distance between the pump and the nozzle may be any distance, for example it may be from 1 to 50 m, notably from 1 to 25 m.

The sufficiently short viscosity recovery time of the gels according to the invention allows the sprayed gels to adhere to all surfaces, for example walls.

The amount of gel deposited on the surface to be treated is generally from 100 to 2,000 $g/m^2$, preferably from 500 to 1,500 $g/m^2$, still preferably from 600 to 1,000 $g/m^2$.

The amount of gel deposited per unit of area and, consequently, the thickness of the deposited gel influences the drying rate.

Thus, when a film is sprayed, a gel layer with a thickness from 0.5 mm to 2 mm on the surface to be treated, the effective contact time between the gel and the materials is then equivalent to its drying time, a period during which the active ingredient contained in the gel will interact with the contamination.

Further, it was surprisingly shown that the amount of deposited gel when it is located in the ranges mentioned above and in particular when it is greater than 500 $g/m^2$ and notably in the range from 500 to 1,500 $g/m^2$, this corresponds to a minimum deposited gel thickness for example greater than 500 µm for a deposited amount of gel of more than 500 $g/m^2$, gave the possibility after drying the gel of obtaining fracturation of the gel as millimetric flakes, for example with a size from 1 to 10 mm, preferably from 2 to 5 mm which are vacuumable (aspirable, suckable).

The deposited amount of gel and therefore the thickness of deposited gel, preferably greater than 500 $g/m^2$, i.e. 500 µm, is the fundamental parameter which influences the size of the dry residues formed after drying the gel and which thus ensures the formation of dry residues with a millimetric size and not of powdered residues, such residues being easily removed by a mechanical method and preferably by suction.

However, it should also be noted that by means of the surfactant at a low concentration, drying of the gel is improved and leads to a homogenous fracturation phenomenon with a mono-dispersed size of the dry residues and increased detachability of the dry residues from the support.

The gel is then maintained on the surface to be treated for the whole time required for its drying. During this drying step, which may be considered as the active phase of the method according to the invention, the solvent contained in the gel, i.e. generally the water contained in the gel evaporates until a dry and solid residue is obtained.

The drying duration depends on the composition of the gel in the concentration ranges of its constituents given above, but also, as this has already been specified, on the amount of gel deposited per unit of area, i.e. the thickness of the deposited gel.

The drying duration also depends on the weather conditions, i.e. temperature, ventilation and relative humidity of the atmosphere in which the solid surface is found.

The method according to the invention may be applied under extremely wide weather conditions, i.e. at a temperature T from 1° C. to 50° C. and a relative humidity RH from 20% to 80%.

The drying time of the gel according to the invention is therefore generally from 1 hour to 24 hours at a temperature T from 1° C. to 50° C. and at a relative humidity RH from 20% to 80%.

It should be noted that the formulation of the gel according to the invention, notably when it contains surfactants such as the "Pluronics®", generally ensures a drying time which is substantially equivalent to the contact time (between the decontamination agent, such as a biocidal agent, and the biological species notably bio-toxic species to be removed) which is necessary, required for inactivating and/or absorbing the contaminating species polluting the material. In other words, the formulation of the gel ensures a drying time which is not other than the inactivation time of the biological contaminating species and which is compatible with the inhibition kinetics of the biological contamination.

The specific surface area of the mineral filler generally used which is generally from 50 $m^2/g$ to 300 $m^2/g$, preferably of 100 $m^2/g$ and the absorption capacity of the gel according to the invention give the possibility of trapping the labile contamination (surface contamination) of the material constituting the surface to be treated.

If necessary, the contaminating biological species are inactivated in the gelled phase. After drying of the gel, the inactivated contamination is removed (eliminated) during recovery of the dry gel residue described below.

Figure 1:
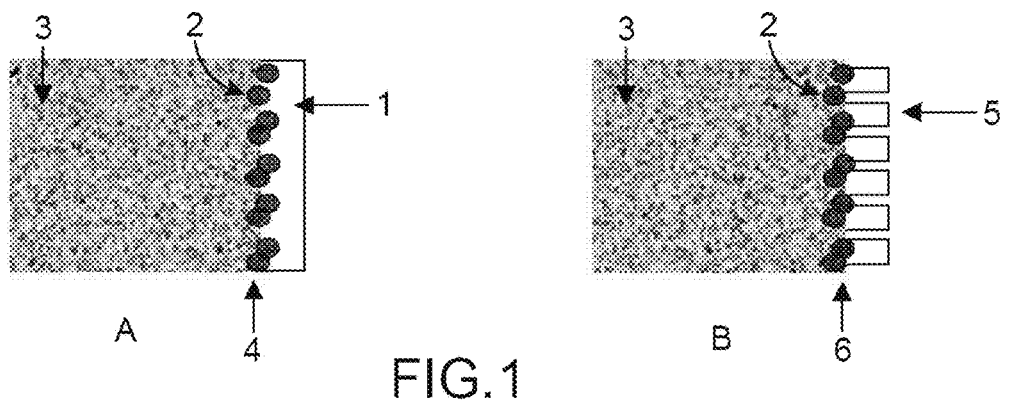
FIG. 1 (A, B) shows schematic sectional views illustrating the main steps of the method according to the invention for decontamination of a solid material.
Figure 2A:
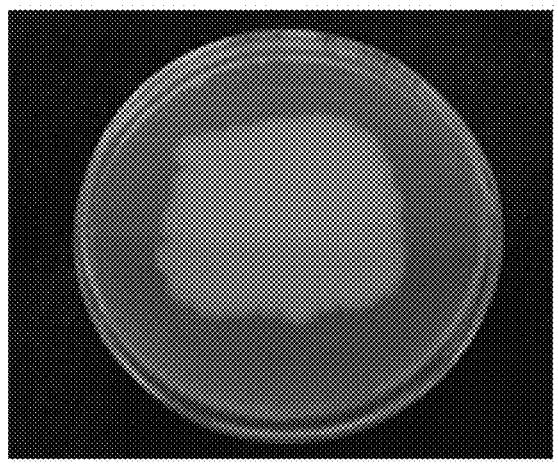
FIG. 2 (A, B, C, D) shows photographs of Petri dishes in which samples have been cultivated, stemming from a stainless steel support initially contaminated with $10^7$ spores of *Bacillus thuringiensis* (similar to *Bacillus anthracis*, a bacteria responsible of anthrax or charbon) and which then was not decontaminated (FIG. 2A) or which was decontaminated with an inactive gel, with water (FIG. 2B), or with a gel of an old formulation (i.e. the gel GB69 with soda and without PSA) (FIG. 2C), or with a gel GB79 according to the invention (FIG. 2D).
Figure 2B:
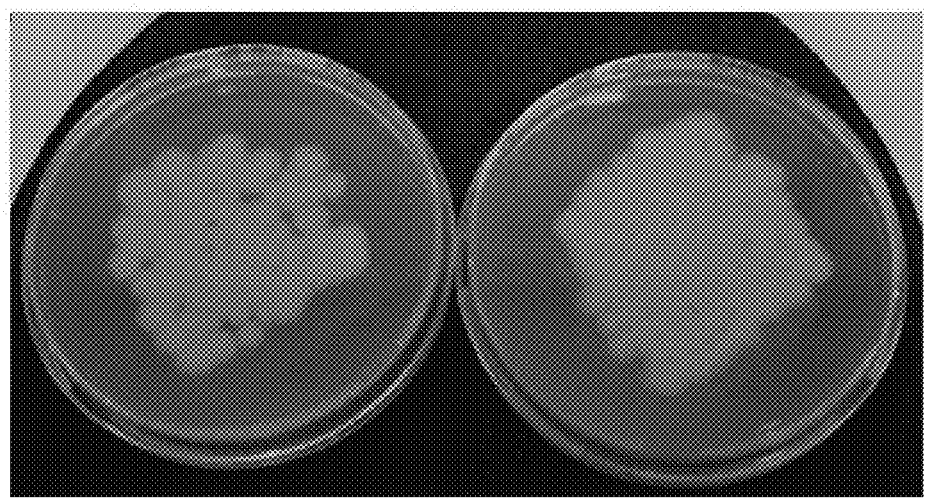
Figure 2C:
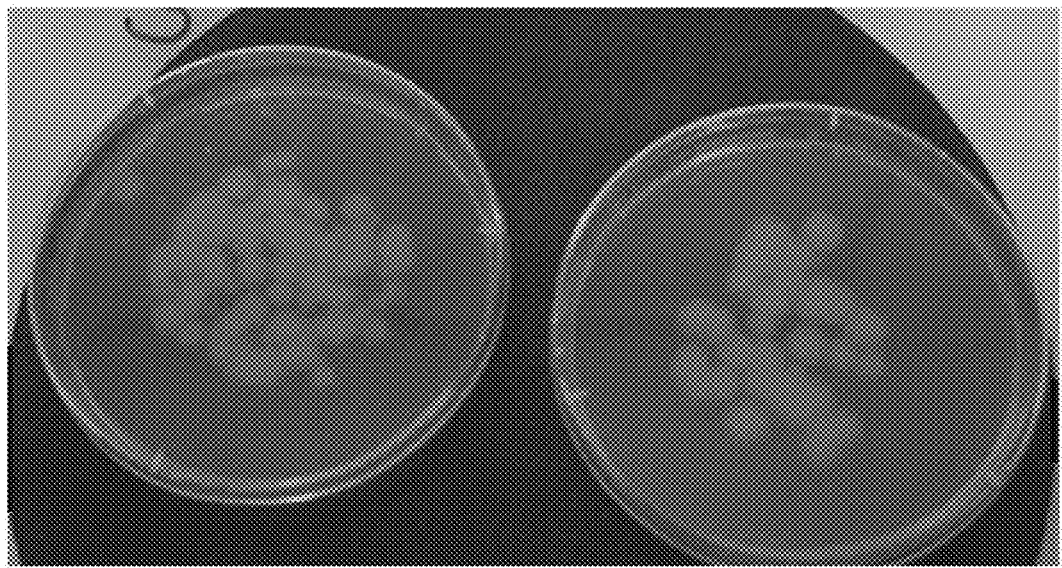
Figure 2D:
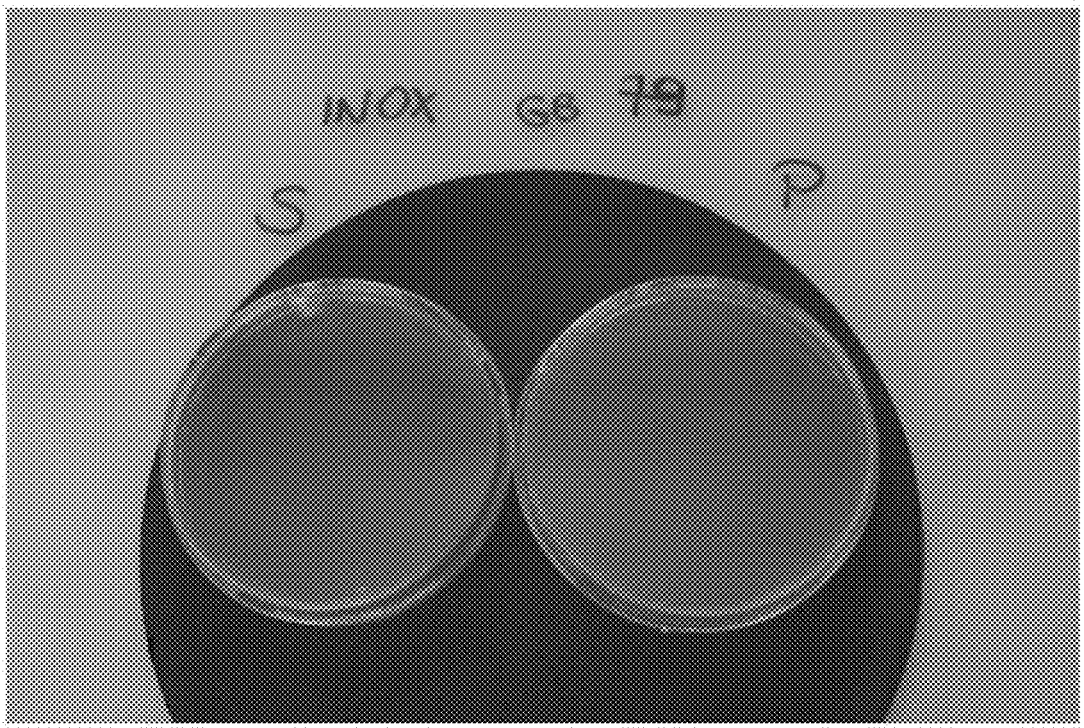

At the end of the drying of the gel, the gel is fractured homogenously so as to give millimetric solid dry residues, for example with a size from 1 to 10 mm, preferably from 2 to 5 mm, non-powdered, generally as solid flakes (5) (FIG. 1B).

The dry residues may contain the inactivated contaminating species (6).

The dry residues, such as flakes (5), obtained at the end of the drying have low adherence to the surface (2) of the decontaminated material. Consequently, the dry residues obtained after drying the gel may easily be recovered by simple brushing and/or suction. However, the dry residues may also be removed with a gas jet, for example a compressed air jet.

Thus, no rinsing is necessary and the method according to the invention does not generate any secondary effluent.

The method according to the invention therefore first of all achieves thereby significant savings in chemical reagents as compared with a decontamination method by washing with a solution. Next, because a waste is obtained as a dry residue which is directly vacuumable, a rinsing operation with water or with a liquid is avoided. Of course this results in a reduction in the amount of produced effluents but also a notable simplification in terms of treatment facility and of outflow.

Because of the majority mineral composition of the gel according to the invention and of the small amount of produced waste, the dry waste may be stored or directed to a discharge facility without any treatment beforehand.

As an example, in the current case when 1,000 grams of gel per $m^2$ of treated surface is applied, the produced dry waste mass is less than 300 grams per $m^2$.

The invention will now be described with reference to the following samples, given as an illustration and not as a limitation.

EXAMPLES

Example 1

In this example, the gels studied in the following Examples 2 to 9 are described.

These gels are the following:
- A comparative gel, non-compliant with the invention, designated as GB70: this is an inactive mineral gel with water, comprising water and alumina.
- A comparative gel, non-compliant with the invention, designated as GB70bis: this is an active mineral gel with water comprising water and alumina like the gel GB70, but for which the viscosity is close to that of active gels.
- A comparative gel, non-compliant with the invention, designated as GB69: this is an alkaline active mineral gel comprising water, soda 1M, alumina, a surfactant and micronized red iron oxide.
- A comparative gel, non-compliant with the invention designated as GBC01: this is an oxidizing alkaline active mineral gel comprising water, soda 1M, sodium hypochlorite, alumina, a surfactant, micronized red iron oxide, and a super-absorbent polymer.
- Gel compliant with the invention designated as GB79: this is an oxidizing alkaline active mineral gel comprising water, soda 1M, sodium hypochlorite, alumina, a surfactant, and micronized red iron oxide, and not comprising any super-absorbent polymer.

The alumina is alumina Aeroxide® Alu C marketed by EVONIK INDUSTRIES with a specific surface area of 100 $m^2/g$ (BET), the surfactant is the surfactant Pluronic® PE6200 marketed by BASF, the soda is soda 1M marketed by SIGMA-ALDRICH, the sodium hypochlorite is sodium hypochlorite with 10 to 15% of active chlorine, marketed by SIGMA-ALDRICH, the super-absorbent polymer is the super-absorbent polymer Aquakeep® produced by SUMITOMO-SEIKA, and the red iron oxide is micronized red iron oxide available under the name of Ferroxide® 212M from ROCKWOOD PIGMENTS LTD, of formula $Fe_2O_3$.

The gel according to the invention designated as GB79 is prepared in the following way: the sodium hypochlorite solution is diluted to 50% with demineralized water. This solution, the surfactant, the iron oxide and the soda are then mixed by means of a mechanical stirrer, provided with a three-blade stirrer, at a rate of 200 revolutions/min, for 3 to 5 minutes. The alumina is then gradually added into the reaction mixture, by gradually increasing the stirring rate as increases the viscosity, in order to attain about 400 to 600 revolutions/min without there being any projections. The gel is then maintained with stirring for 5 minutes.

The other gels are prepared in a similar way.

The composition of the different studied gels is given in Table 1 below.

TABLE 1

Composition of the different studied gels.

| Nature of the gel | Composition | Mass percentages (%) |
|---|---|---|
| GB70 | $H_2O$ | 86 |
| (Inactive gel with water) | Alumina | 14 |
| GB70bis | $H_2O$ | 78.8 |

TABLE 1-continued

Composition of the different studied gels.

| Nature of the gel | Composition | Mass percentages (%) |
|---|---|---|
| (Inactive gel for which the rheology is close to those of active gels) | Alumina | 21.2 |
| GB69 | NaOH 1M | 85.7 |
| (Active gel with soda, as a comparison) | Alumina | 14 |
| | Pluronic ® PE6200 | 0.2 |
| | Iron oxide 212M | 0.1 |
| GBC01 | NaOH 1M | 41.925 |
| (Comparative active gel 50:50 Soda:Bleach ("Javel") and Aquakeep ®) | 50% diluted sodium hypochlorite (10-15% a.c.) | 41.925 |
| | Alumina | 14 |
| | Pluronic ® PE6200 | 2 |
| | Iron oxide 212M | 0.1 |
| | Aquakeep ® | 0.05 |
| GB79 | NaOH 1M | 42.45 |
| (Active gel 50:50 Soda:Bleach ("Javel"), according to the invention) | 50% diluted sodium hypochlorite (10-15% a.c.) | 42.45 |
| | Alumina | 14 |
| | Pluronic ® PE6200 | 1 |
| | Iron oxide 212M | 0.1 |

Example 2

In this example, the improvement in the biocidal efficiency of the soda-bleach gel GB79 according to the invention is shown as compared with the comparative gel GB69 which only contains soda.

In this example, in order to compare the biocidal effectiveness of both of these gels, experiments are conducted in a microbiology laboratory L2 under sterile conditions—i.e. in a laminar flow hood—on a simulation of *Bacillus anthracis*, i.e. spores of *Bacillus thuringiensis* (B.t.).

Various stainless steel supports are cleaned and passed into the autoclave.

Two of them are dirtied, polluted, artificially in order to attempt to reproduce a used material as accurately as possible. This dirt, pollution, is formed by a mixture of 1% of clay (Montmorillonite available from SIGMA-ALDRICH under the name of "Aluminum Pillared Clay"), of 10% of engine oil 15W40, and of ethanol for the balance.

Next, all the supports are contaminated with a liquid deposition of 100ℓ of a solution with $2\times10^8$ spores of *Bacillus thuringiensis* (B.t.) per mL, i.e. a deposit of $2\times10^7$ spores of B.t. which are left to dry completely (about 30 minutes).

The gel to be tested is then applied according to a volume calculated according to the surface area of the supports in order to have an applied gel thickness of 0.7 mm. The supports are thus put to dry in closed Petri dishes until complete drying of the gel (3-5 hours depending on the temperature of the laboratory).

Next, the flakes are recovered in a Falcon tube by brushing, in a known amount of nutrient medium Luria-Broth (LB). Also, the supports are placed in a known volume of LB in a Falcon tube. The whole of the Falcon tubes are then vortexed, and then placed in an incubator for 1 h at 30° C. with stirring.

Subsequently, the Falcon tubes containing flakes are centrifuged (3 min, 4,500 rpm).

Next, for each of the tubes, a range of dilutions to one-tenth is produced from the supernatant. Finally, 1 mL is sampled from each of the tubes of each range of dilutions. The sample is then deposited at the bottom of an empty and sterile Petri dish. LB gelose medium is then poured in the dish (bulk sowing). These dishes are then placed in the incubator at 30° C. for 24 hours. The colonies in the dishes are then counted one by one, and then for each sample (support or flakes from which the range of dilutions was made), an average of living spores is calculated. Finally, the various dilutions are taken into account in order to obtain the total number of living spores present on the support or in the flakes. The decontamination factor may then be calculated by determining the reduction (abatement) in thousands of killed spores ($\log_{10}$).

In this example, as the goal was to compare the biocidal efficiency of the biocidal gel GB79 according to the invention with the comparative gel GB69, the gels GB70bis (inactive gel with water), GB69 (comparative gel) and GB79 (gel according to the invention) are tested according to the procedure described above.

Figure 3:
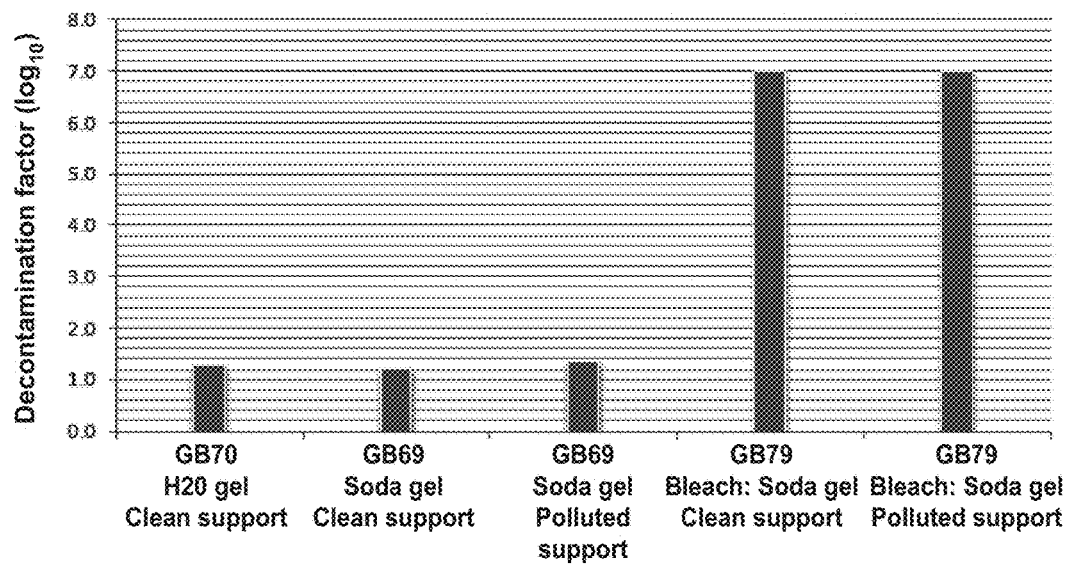
FIG. 3 is a graph which compares the biocidal efficiency, expressed by the decontamination factor ($\log_{10}$), of different gels on the stainless steel supports either clean or polluted (with a mixture of Montmorillonite clay, engine oil 15W40 and ethanol (similar to used and dirty supports)), contaminated with spores of *Bacillus thuringiensis*, i.e. from left to right the gel GB70 which is an inactive gel with water, on a clean support; the gel GB69 which is a gel with soda, on a contaminated clean support; the gel GB69 on a contaminated polluted support; the gel GB79 which is a gel with soda and with bleach ("Javel") according to the invention, on a contaminated clean support; the gel GB79 which is a gel with soda and with bleach according to the invention, on a contaminated polluted support.

The results of these experiments are illustrated in FIG. 3 where appears the decontamination factor obtained on stainless steel supports versus the gel used (also see FIGS. 2A, 2B, 2C, 2D).

On this histogram, it appears that the comparative gel GB69 has the same biocidal effectiveness as the gel without any active decontamination agent, i.e. the gel with water GB70bis. On the other hand, the gel according to the invention GB79, has both on a clean support and on a polluted support, a biocidal efficiency of a minimum of 7 log. Indeed, no residual living spore was detected during counts on the $2\times10^7$ spores initially deposited. The decontamination of the surface to be treated with the gel according to the invention, for which the biocidal activity is reinforced is therefore efficient even on a polluted support, thereby showing its strong degreasing power.

Example 3

In this example, the incompatibility between the oxidizing agent and the super-absorbent polymer is shown.

In the biocidal gel formulation of document [1], poly (sodium acrylate) which is a super-absorbent polymer, was added in order to improve the efficiency of the biocidal gel on porous materials such as mortars. Indeed, this adjuvant allows prolonged release of the decontamination active ingredient. However, the rheology of this type of gel are strongly modified to the point of becoming very compact. The contact then becomes very bad on the surfaces to be decontaminated.

In this example, the biocidal efficiency of two gels containing beach and soda are first of all compared. The first gel is a gel according to the invention, formulated without any super-absorbent polymer (GB79), the second is a comparative gel which contains an absorbent polymer (GBC01), and which was stored for more than 30 days.

The biocidal efficiency is exactly evaluated according to the same procedure as in Example 2, except that the initial contamination in deposited spores is $2\times10^7$ for the supports treated with GB79 gel, and of $7.5\times10^6$ for the supports treated with the gel GBC01.

The supports treated by the gels are stainless steel supports (called INOX supports) and supports formed by ceramic tiles of the type which coat the walls of the Paris metro stations and which are provided by the RATP (called RATP supports).

Figure 4:
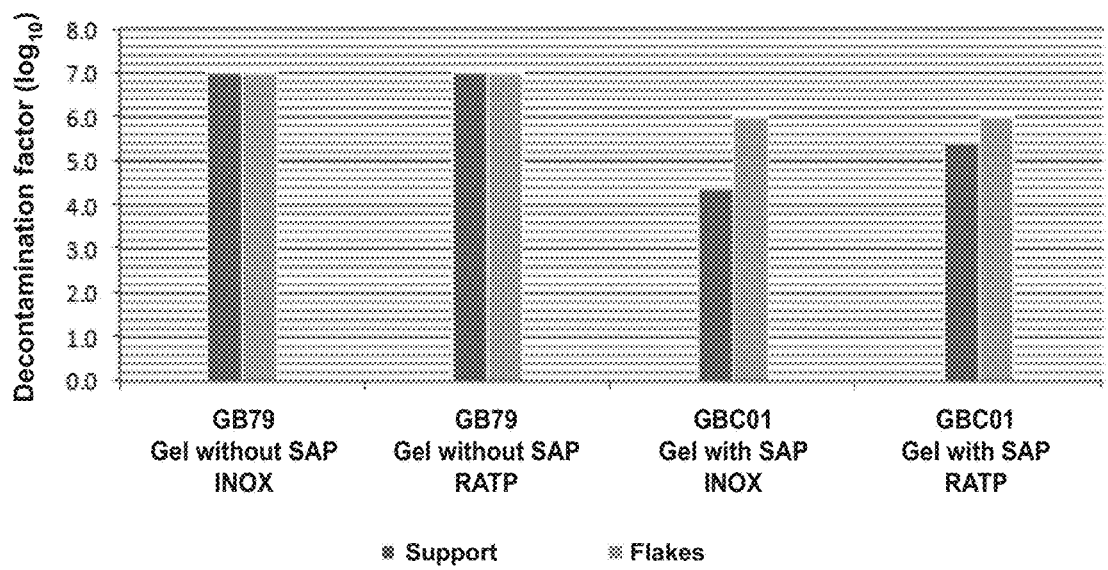
FIG. 4 is a graph which compares the biocidal efficiency, expressed by the decontamination factor ($\log_{10}$) of gels without (GB79) and with a superabsorbent polymer (PSA) (GBC01) on a stainless steel support or on a support which is a ceramic tile provided by RATP, i.e. from left to right the gel GB79 and then the gel GBC01.

The results, illustrated in FIG. 4, show a lowering of the biocidal efficiency for the gel containing the super-absorbent polymer (PSA), for which, however, the supports were slightly less contaminated.

Indeed, with the gel without any PSA according to the invention (GB79), the INOX and RATP supports are decontaminated by at least 7 log, i.e. the initial deposited amount.

On the other hand, with the gel containing a PSA (GBC01), the decontamination of the supports attains with difficulty 5 log, while being aware that the initial contamination was lower.

It should also be noted that in every case, the flakes did not contain any detectable living spore.

The rheology of the gel according to the invention, formulated without any super-absorbent polymer (GB79), and of the comparative gel which contains an absorbent polymer (GBC01) are subsequently studied.

More particularly, the threshold stress and the viscosity of the gels GB69, GB79, fresh GBC01 (which has just been prepared) also called new gel, and GBC01 having been stored for more than one month, also called old gel.

The measurement of the viscosity versus the shearing rate is conducted by means of a Rheomat® RM100 viscosimeter from LAMY RHEOLOGY. The viscosimeter is equipped with a measurement system of the anchor type MS-R3. After pre-shearing for 10 seconds at a shearing rate of $1\ s^{-1}$, 15 shearing rate plateaus ranging from $1\ s^{-1}$ to $100\ s^{-1}$ are carried out with measurement of the viscosity every 20 seconds.

The measurement of the threshold stress is conducted by means of a rheometer TA Instruments AR-1000 in a "Vane" geometry. A low shearing rate ($6.7\times10^{-3}\ s^{-1}$) is applied to the gels in a constant way in order to deform them from rest and thus determine their flow threshold.

Figure 5:
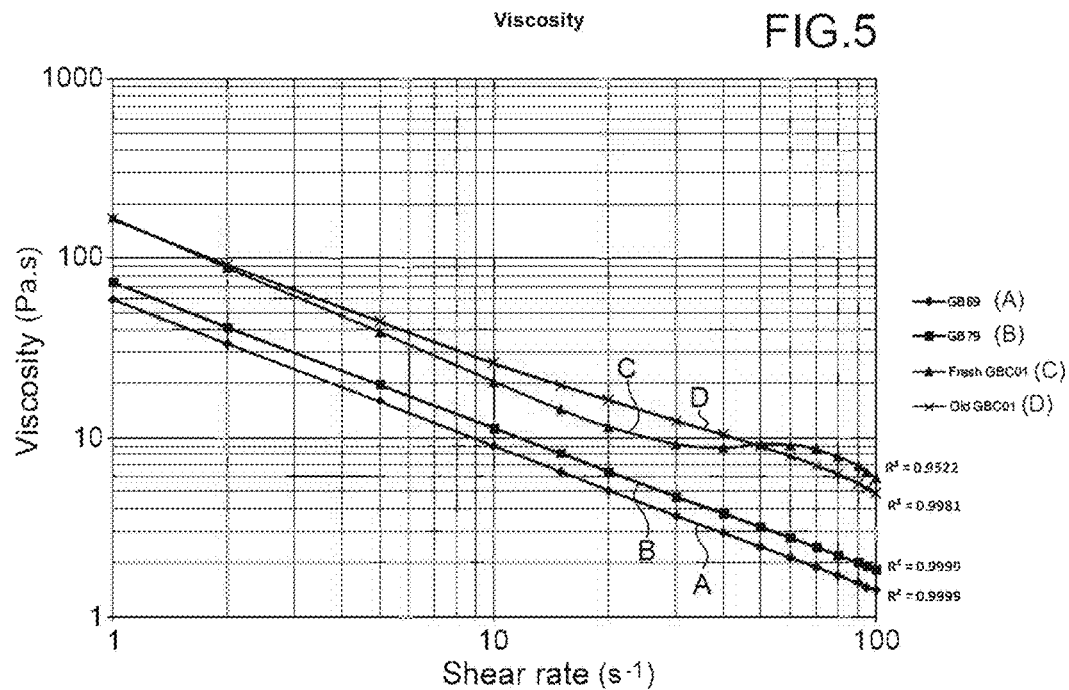
FIG. 5 is a graph which gives the viscosity (in Pa·s) versus the shear rate (in $s^{-1}$) for the gels GB69 (♦) (curve A), GB79 (■) (curve B), fresh GBC01, which has just been prepared, also called a new gel (▲) (curve C), and GBC01 having been kept for more than one month, also called an old gel (x) (curve D).
Figure 6:
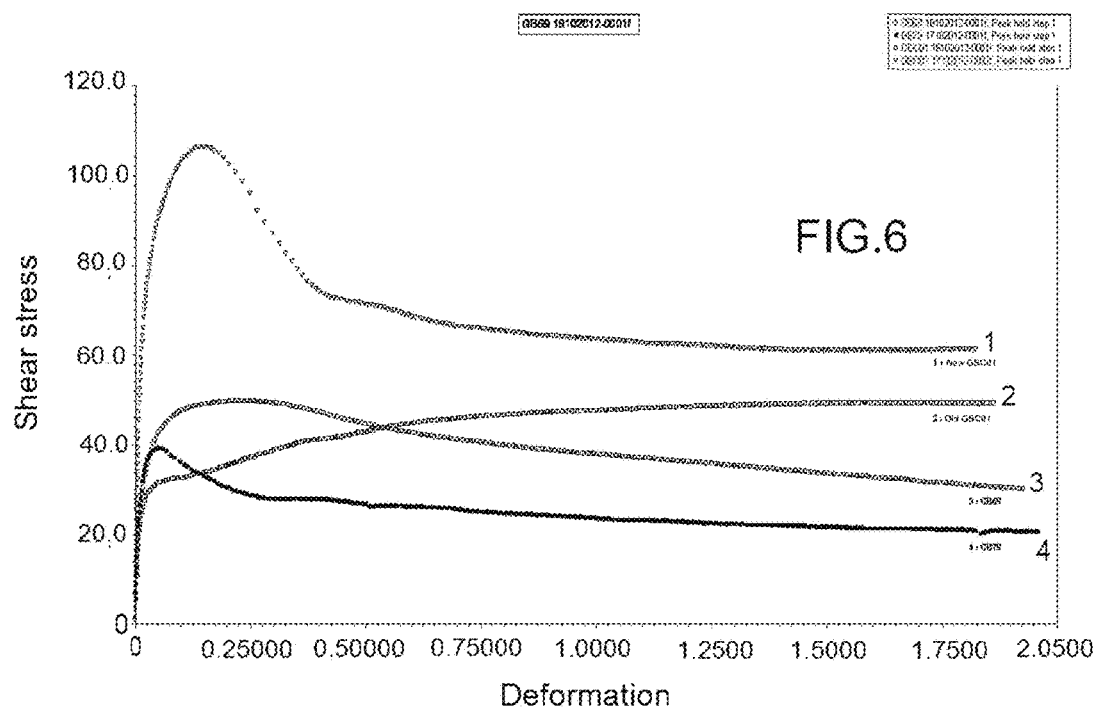
FIG. 6 is a graph which gives the shear stress (in Pa) versus the deformation for the new gel GBC01 (curve 1), the old GBC01 gel (curve 2); the gel GB69 (curve 3); and the gel GB79 (curve 4).

The results are illustrated in FIGS. 5 and 6.

In FIG. 5, which illustrates the viscosity versus the shearing rate in a logarithmic scale, it appears that both curves of the gels GB69 and GB79 according to the invention, without any super-absorbent polymer are very close and parallel. Moreover they are linear which corresponds to the rheological behavior of rheofluidifying fluids with a threshold stress.

On the other hand, for both fresh and stored gels GBC01 which contain a PSA, the curves are not linear (cf. regression coefficients) which characterizes a less ideal and predictable rheological behavior than that of the gel according to the invention without any super-absorbent polymer.

FIG. 6 illustrates the shearing stress versus the deformation for each of the gels. In every case, two schemes may be noted. First of all the stress increases linearly, the material is in a solid scheme (elastic deformation). A change in behaviour is then observed, the stress attains the flow threshold and the material passes to a liquid scheme (stationary flow). The threshold stress corresponds to the stress at the flow threshold, i.e. a 106.5 Pa for the new gel GBC01 (curve 1), 49.35 Pa for the stored GBC01 gel (curve 2), but the aspect of which is not compliant with standard profiles and the value of which is strongly questionable, 49.69 Pa for the gel GB69 (curve 3) and 39.13 Pa for the GB79 gel (curve 4).

This example therefore gives the possibility of showing that with the biocidal gel according to the invention, it is possible to do without the presence of a super-absorbent polymer, such as poly(sodium acrylate), since it does not visibly improve the efficiency of the biocidal gel while altering its flow properties, indeed the gel which contains a PSA is a highly viscous gel, for which the rheofluidifying behavior is not very predictable, notably after several days of storage after which the measurement of a threshold stress becomes impossible.

Example 4

In this example, the biocidal efficiency of the gel GB79 according to the invention is shown on various supports made of diverse materials.

In this example, the biocidal efficiency is evaluated according to the procedure of Example 2, except that the initial contamination is $2\times10^7$ spores of B.t. deposited on all supports, except on the two plastic supports where it is $2\times10^6$.

Further, all the supports are clean. The various tested supports are the following: a glass support (called VERRE support), a stainless steel support, a support consisting of a ceramic tile provided by the RATP, a mortar support, a PVC (polyvinyl chloride)) support, and a PVDF (poly (vinylidene fluoride)) support.

Figure 7:
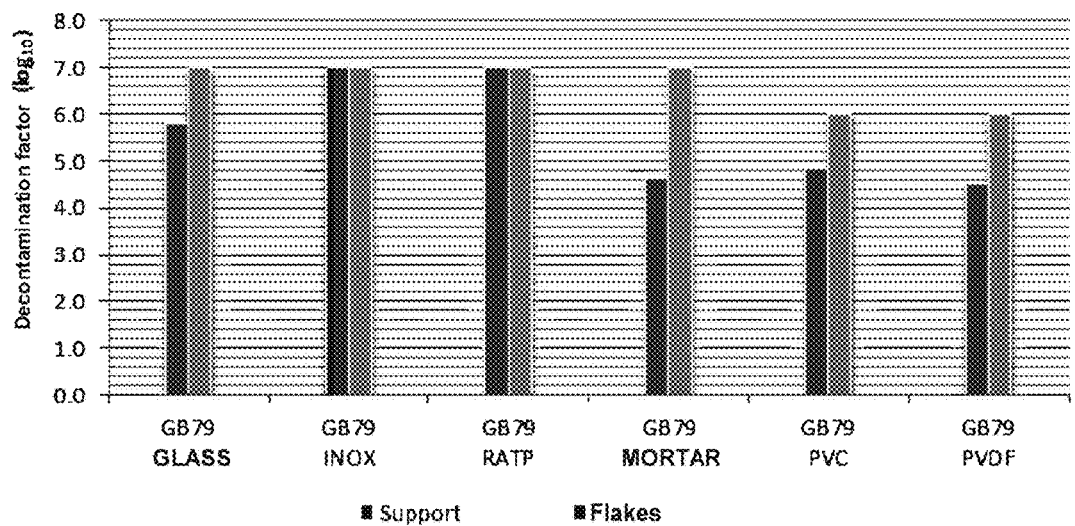
FIG. 7 is a graph which gives the biocidal efficiency, expressed by the decontamination factor ($\log_{10}$), of the gel GB79 which is a gel with soda and with bleach according to the invention on clean supports in different materials, i.e. from left to right: a glass support (called a VERRE support), a stainless steel support (called INOX support), a ceramic tile provided by RATP (called RATP support), a mortar support (called MORTIER support), a PVC support (polyvinyl chloride), a PVDF support (polyvinylidene fluoride). On this graph for each support, in addition to the decontamination factor obtained for support (left bar), is also plotted the decontamination factor obtained in dry residues, flakes (right bar).

The results are shown in FIG. 7. They show that the supports in non-porous materials (VERRE, INOX and RATP supports), the decontamination of the supports attains a minimum of 6-7 log.

On the supports in mortar and the supports in plastic materials, nearly 5 log of spores are killed (let us remind you that in Example 2, on stainless steel supports, the decontamination did not attain 2 log with the gel GB69 with soda). As regards the dry residues, i.e. the flakes, in every case, no residual spore is detectable.

Example 5

In this example, the absence of living spores in the dry residues, the flakes, is demonstrated.

More exactly, in this example, it is shown that no residual spore is actually found in the flakes, i.e. no living spore is confined in the flakes without being to appear upon counting since they would be trapped in the latter and would not migrate in the LB medium.

To do this, on two clean RATP supports, and always according to the procedure detailed in Example 2 (except for the initial contamination which consists here of a deposit of $10^6$ spores of B.t.), drying of the gel according to the invention GB79 is carried out.

At the end of the drying, on the first support, the flakes are recovered conventionally by brushing in a known amount of LB medium.

On the second support, the flakes are brushed and then finally milled with a mortar in order to be put into contact with the LB medium. The sequence of the procedure is then conventional, i.e.: incubation for 1 h at 30° C., "vortex," centrifugation, ranges of dilutions, counting dishes, incubation for 24 h at 30° C. (cf. procedure of Example 2).

Figure 8:
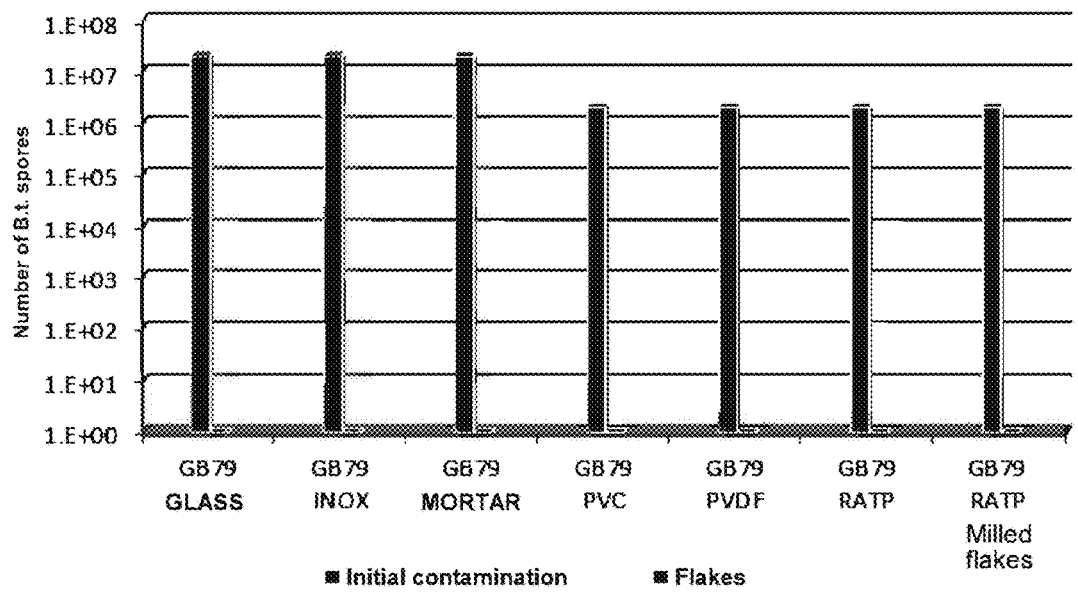
FIG. 8 is a graph which gives the detectable biological activity expressed in the number of spores of B.t (*Bacillus thuringiensis*), in dry residues, flakes, obtained after drying the gel GB79 which is a gel with bleach and with soda according to the invention on clean supports in different materials, i.e. from left to right: a glass support (called VERRE support), a stainless steel support (called INOX support), a mortar support (called MORTIER support), a PVC (polyvinyl chloride) support, a PVDF (polyvinylidene fluoride) support, a support which is a ceramic tile provided by RATP, and finally a support which is a ceramic tile provided by RATP, the flakes having been finely milled.

The results of the counts on both of these series of flakes are illustrated in FIG. 8 and are confronted with the results of the previous experiments on different clean materials. Regardless of the material, no living spore is detectable in the flakes. This is also again confirmed when the flakes are finely milled (last bar of the histogram).

Example 6

In this example, the action kinetics of the gel according to the invention GB79 are shown. To do this, different experiments were carried out on 10 clean supports made of RATP ceramic.

The initial contamination of the supports is $10^7$ spores of B.t. per support.

The same experiment is carried out with a gel with water GB70bis.

The gels are applied on various supports at time T0=0 minutes.

Next, the gels in a drying phase, or even in a fracturation phase, are recovered after 0 min, 10 min, 20 min, 30 min, and 1 h.

During each recovery operation, the gel and the support are recovered in known amounts of culture medium LB before following the conventional treatment, i.e.: incubation, vortex, centrifugation, range of dilutions, counting dishes, incubation for 24 h at 30° C. (cf. procedure of Example 2).

The results are shown in FIG. 9. It appears that the active gel GB79 according to the invention decontaminates the support by more than 3 log in the first 10 minutes, and that, after a complete drying time of 210 minutes, this gel decontaminates with an efficiency of at least 7 log.

These results may be compared with the results obtained during the same experiment carried out with an inactive gel with water in which no decontamination is notable overtime.

As regards the flakes of the gel GB79, it appears that after 10 minutes, no residual spore is detectable. This confirms again the results obtained in Example 5. Indeed, from 0 to 60 minutes, the gel is not yet fractured and is humid. It is therefore easy to put it back into solution homogenously in the nutrient medium LB during its recovery in order to count the number of living spores. The results show once again that the gel is totally in solution in the LB and that no spore is detected therein, no residual living spore is able to escape detection because of its confinement in the solid network formed by the flakes (which are very poorly dissolved once total dryness is completely attained), and the recovered flakes are therefore not contaminated.

Example 7

In this example, it is shown that the gel GB79 according to the invention is particularly well adapted to application by spraying.

The rheological study of the gel GB79 gives the possibility of measuring its threshold stress which is 39.13 Pa (cf. Example 3, FIG. 6).

Thus, it appears that the gels according to the invention for which the active ingredient is a mixture of bleach and of soda meet the requirements of "vacuumable gels," i.e. a threshold stress of more than 15-20 Pa so that the gel does not flow under the effect of gravity on a vertical wall for thickness from 0.5-2 mm.

Moreover, the viscosity of the gel according to the invention (cf. Example 3, FIG. 5) is totally similar and very close to that of the gel with soda GB69 which was already tested by application with spraying. The gel according to the invention is therefore compliant with the requirements specification of a "vacuumable gel" from a rheological point of view.

Example 8

In this example, it is shown that the gel according to the invention may actually be defined, in terms of drying and fracturation kinetics, as a "vacuumable gel," i.e. it dries within a reasonable time, for example of a few hours, and that it fractures by producing non-powdery flakes.

These two features of "vacuumable gels," and more particularly the drying kinetics, are closely related to the weather conditions of the drying environment, i.e. the temperature, the relative humidity and the ventilation/aeration.

In this example, both gels GB69 (gel with soda) and GB79 according to the invention (gel with bleach and soda) are put to dry one after the other in a weathering chamber Binder® adjusted to 25° C. and to 50% of relative humidity.

The gels are spread out over machined stainless steel nacelles (boats) so as to obtain a controlled thickness of 0.5 mm of gel in the nacelle.

In the weathering chamber, precision scales Sartorius® are installed, as well as a camera Moticam® surrounded by a circular LED lamp (VWR®) which is placed on the top of the scales. The scales and the Moticam® camera are connected to a computer placed outside the weathering chamber, which thus allows simultaneous acquisition, during drying in a controlled atmosphere, of the mass and of the images of the nacelle filled with gel.

It should be noted that the nacelle containing the gel is placed in the position scales, and that all the doors of the scales are closed, except for the door opposite to the fan, which is opened by 3 cm in order to maintain a controlled atmosphere in the chamber of the scales while limiting the air flow related to the operation of the weathering chamber.

By recording the mass during the drying, it is then possible to plot a curve illustrating the drying kinetics, while the analysis of the images by means of a piece of software for processing images of the totally dry gel allows automatic detection of the flakes and their counting as well as calculation of their area.

The results are shown in FIGS. 10 and 11.

The results, shown in FIG. 10, show mass loss curves completely parallel between both gels which attain total dryness within 5 hours (300 min) under temperature and relative humidity conditions. Indeed, within 260 to 300 minutes, the gels GB69, and GB79 according to the invention, respectively lose 78% and 73% of their initial mass. The addition of sodium hypochlorite to the formulation therefore has no impact on the total drying time of the gel which remains widely applicable according to the "vacuumable gel" method with the gel according to the invention GB79.

As regards fracturation, the results of which are summarized in FIG. 11, it appears that the number of flakes is less significant for flakes from the gel GB79 according to the invention containing sodium hypochlorite. The flakes for this gel GB79 according to the invention are on average larger but remain millimetric (4 $mm^2$ on average). This gel therefore remains adequate for the targeted application since it produces non-powdery flakes with millimetric size.

Example 9

In this example, the harmlessness of the gel according to the invention GB79 is shown on different materials.

More exactly, in this example, it is shown that the gel according to the invention may be applied on many materials without altering either the mechanical properties or the physical integrity thereof.

To do this, the surface condition, and notably the roughness, of different materials, is compared for non-treated surfaces, surfaces on which the inactive gel with water GB70bis has dried, or further surfaces treated with the oxidizing alkaline gel according to the invention GB79.

A STIL (Sciences et Techniques Industrielles de la Lumiére) profilometer is used for plotting the profiles and measuring the average roughness on the surfaces of parts, supports made of these different materials.

The surface of each tested material is divided into three portions: the portion on which dries the gel with water GB70bis, the second on which nothing is applied and the third on which dries the gel GB79. Once the gels are totally dry, the supports are cleared of the flakes and properly cleaned before making measurements with the profilometer. The tested materials are the following: stainless steel, copper, lead, painted steel, glass, ceramic, RATP, HDPE (high density polyethylene), PC (polycarbonate), PMMA (poly (methyl methacrylate)), PP (polypropylene), PU (polyurethane), PVC (polyvinyl chloride), PVDF (polyvinylidene fluoride) and rubber.

The results are shown in FIGS. 12 (A, B, C), 13, and 14.

FIG. 12 illustrates the 3D mapping and the obtained profile with the optical profilometer of a stainless steel support. It is seen that there is no modification of the roughness (of the profile) between the portion which was treated with the oxidizing alkaline gel (left 3D mapping (FIG. 12A)) and the left portion of the profile before separation (FIG. 12C) and the non-treated portion, having remained intact (3D mapping on the right (FIG. 12B)) and the right portion of the profile after separation (FIG. 12C).

FIGS. 13 and 14 represent in a condensed way the results of these measurements with the optical profilometer on the whole of the materials. In order to obtain these curves, the average roughness was measured on a portion of the sample, for which the surface includes three areas, the first treated with the inactive gel with water, the second not treated, and the last treated with the gel according to the invention. For the whole of the materials, no alteration of the surface is observable with the naked eye. The measured roughness remains relatively constant for the different materials on the treated and non-treated surfaces.

Example 10

In this example, the preservation of the biocidal activity is evaluated after storing the gel according to the invention GB79.

In order to evaluate the preservation of the biocidal activity following storage of the gel GB79, two different experiments are conducted.

The first experiment consists of re-evaluating the biocidal efficiency of the gel GB79 on spores of *Bacillus thuringiensis* according to the procedure discussed in Example 2 after 3 months of storage, preservation, at room temperature, without the gel being protected from light, and of comparing the thereby obtained results, with those obtained 3 months earlier with the same gel freshly made. This experiment was conducted on supports consisting of ceramic tiles provided by the RATP.

The second consists of measuring the percentage of active chlorine present in the gel in order to evaluate its degradation rate during storage. For this, a fresh gel was made and then stored away from light in the laboratory. In the same way, the commercial sodium hypochlorite solution used (10-15% a.c.) is stored in the refrigerator and in the laboratory. Regularly, a small amount of this gel and of this solution are recovered and dissolved in distilled water. The sodium hypochlorite is then conventionally dosed by dosage with return of the di-iodine (formed by addition of potassium iodide) with sodium thiosulfate.

The results from the test on spores of B.t. are shown in FIG. 15. After 3 months of storage, the gel remains as active as the freshly prepared gel.

As regards the dosage of sodium hypochlorite in the gel, the results of which are shown in FIG. 16, it appears that over more than one month of storage, the percentage of active chlorine (a.c.) is slightly affected. Indeed, a slight reduction in the active chlorine percentage in the gel is observed, which should be monitored in order to ensure that it is not significant. Nevertheless, considering the results obtained by testing the biocidal efficiency on B.t. after 3 months of storage of the gel, this slight decrease in the percentage of active chlorine in the gel does not seem to affect the biocidal efficiency of the reinforced formulation.

This example shows that the gel according to the invention may be stored after its preparation with view to subsequent application if need be.

Example 11

In this example, the bleeding of the gel according to the invention is evaluated.

Indeed, another phenomenon is important to consider in the case of storage of the gel with view to subsequent use is its bleeding, i.e. the sedimentation caused by a long storage and which optionally requires that the product be again homogenized before its use.

In order to evaluate this phenomenon, 90 g of the gel GB79 according to the invention are stored without being used or homogenized. The amount of supernatant is regularly measured overtime in order to quantify this phenomenon. In the same way, this measurement is conducted for the gel GB69 in order to see the possible impact on the bleeding of the addition of sodium hypochlorite to the formulation.

The results are shown in FIG. 17. It appears that, certainly the gel according to the invention GB79 is also victim of this phenomenon to an amount of 3.3% in three months, but this phenomenon is visibly more significant on the gel GB69 which attains a bleeding of more than 5% in three months.

The bleach/soda gels according to the invention therefore have a similar or even superior capacity for storage, than the gels of the old formulation.

Conclusion of Examples 1 to 11

As regards the Examples shown above, it appears that the gel according to the invention notably because of the addition of sodium hypochlorite is an efficient product both as regards its formulation and its application within the scope of biological decontamination.

Indeed, the biocidal activity of the gel according to the invention is reinforced relatively to a gel only containing soda as a biological decontamination agent, since it gives the possibility of attaining decontamination factors on simulations of anthrax spores of at least 6 log while avoiding the addition of a super-absorbent polymer which made the gel of document [1] unsuitable for a use by spraying after storage.

Moreover, the gel according to the invention may be stored and then used according to the so called "vacuumable gel" concept of use since the viscosity and its threshold stress remain adapted to application by spraying on horizontal or vertical walls and that the gel dries and fractures into non-powdery millimetric flakes within a reasonable time and adapted to an intervention of the post-event type subsequent to a malicious biological attack.

In Examples 12 to 15 which follow, the gel GB79 according to the invention is tested on actual pathogenic biological agents in order to show its efficiency on real agents of the NRBC threat.

With this purpose, test aiming at showing the efficiency of the gel GB76 according to the invention were conducted on supports contaminated with ricin (toxin), spores of *Bacillus anthracis* (B.a.) (anthrax, charbon), bacteria *Yersinia pestis* (Y.p.) (plague) and the virus of vaccine.

Example 12

In this example, the decontaminating efficiency of the biocidal gel GB79 according to the invention on a pathogenic biological agent of the plant toxin type, ricin. This toxin, a by-product of the treatment of ricin seeds, inhibits the cells responsible for synthesis of proteins in the organism, and may thus cause death.

The efficiency of the gel on ricin was tested on contaminated glass slides per 10 μL of different solutions of ricin (more or less concentrated) (see FIG. 18).

Cytotoxicity tests (cf. procedure hereafter) were conducted on Vero cells in order to detect the activity of ricin with and without application of the biocidal gel (ricin prevents cells from making more or less a protein).

The results of these tests are shown in FIG. 19.

Curve A, in a solid line, with points ● shows the effect of liquid ricin at various concentrations on these cells.

Curve B, in dotted lines, points ■ shows the effect of dried ricin (like on the test slides) at various concentrations on these cells.

Curve C, in dash lines, points ▲, show the effect of ricin subsequent to the use of the GB79 gel on ricin.

It is observed that the gel is capable of efficiently inactivating ricin on glass (at least by a factor 1000: no lethality (and therefore no loss of synthesis of protein) when the gel is applied on ricin).

Finally, the points ◆ represent the flakes but unfortunately the residual toxicity of the flakes alone (without ricin) has a significant lethal effect on the cells and these results are therefore not representative of the possibly active ricin in the flakes.

Example 13

In this example, the efficiency of the biocidal gel GB79 according to the invention is tested on supports contaminated with spores of *Bacillus anthracis* (B.a), bacteria *Yersinia pestis* (Y.p) or further the virus of vaccine. The tests are carried out under reference conditions.

The supports used are clean coupons in stainless steel (INOX) and ceramic tiles (RATP) of 5 cm×5 cm.

The tests conducted under the reference conditions are tests conducted on clean materials at room temperature, i.e. around 20° C., and at 40% of relative humidity.

The tests are conducted according to the following procedure:

1) contamination of the supports (which are positioned horizontally in Petri dishes throughout the test) by depositing with the micropipette a 100 μL of bacterial or viral suspension as droplets;

2) drying of the contamination;

3) deposition by means of a pipette of about 2 to 3 mL of GB79 gel according to the invention on the coupons, and then spreading out the latter by means of sterile plastic spreaders;

4) drying the gel at the recommended temperature for the test. This test has to be maintained until complete drying of the gel;

5) recovery of the dried gel particles in a Petri dish;

6) taking swabs from the totality of the surface of the supports by means of a humidified swab;

7) extraction of the swabs in 2 mL of sterile water for the bacteria, or of the culture medium for viruses, by vortex stirring;

8) "wiping" the extracted swabs on a gelose culture medium (a step which is not carried out for viruses, since vaccine cannot be cultivated on a "solid" medium);

9) producing an "imprint" of the swabbed supports by means of gelose-contacts (not carried out for viruses);

10) re-suspending the whole of the dried gel particles in 4 mL of water for bacteria, or 2 mL of culture medium for viruses, and then extraction by vortex stirring;

11) counting the micro-organisms contained in each of the recovered suspensions during the test, by cultivation on/in a suitable medium for the tested biological agent.

For each test, 5 supports—coupons or tiles—of tests are made as well as 3 supports—control coupons or tiles. The control supports are subject to the same steps as the test supports, except for the decontamination with the gel and all the steps which are related thereto.

Thus, only the steps nos. 1, 2, 6, 7 and 11 are applied to them. The supports are also subject to the same conditions as the test supports during the drying of the gel (notably for example the temperature, the hygrometry and waiting times conditions).

The results are shown in Table. It appears that regardless of the pathogen, the supports are perfectly decontaminated, since we are below the detection limits of the micro-organisms. As regards the flakes, they are not contaminated in the whole of the cases, except for one case, when the flakes contain very few anthrax spores (as compared with the $2.4.10^6$ spores initially deposited). It should be noted that under these ambient conditions of temperature and of relative humidity, the gel takes about between 4 h and 6 h for completely drying under a MSS (Microbiological Safety Station) in open Petri dishes.

TABLE 2

Efficiency of the biocidal gel according to the invention on pathogenic agents (reference conditions).

| Agent | Support | Temperature (° C.) | Initial contamination of the support (CFU/PFU) (1) | Final contamination of the support (CFU/PFU) | Residual contamination of the flakes (CFU/PFU) |
|---|---|---|---|---|---|
| B. anthracis (spores) | Stainless steel | ~20 | $7.4.10^6$ | < d.l. (2) | < d.l. |
| | RATP ceramic | ~20 | $2.4.10^6$ | < d.l. | 68 |
| Y. pestis (bacteria) | Stainless steel | ~20 | $1.2.10^6$ | < d.l. | < d.l. |
| | RATP ceramic | ~20 | $4.1.10^6$ | < d.l. | < d.l. |
| Vaccine (virus) | Stainless steel | ~20 | $8.8.10^4$ | < d.l. | < d.l. |
| | RATP ceramic | ~20 | $4.4.10^4$ | < d.l. | < d.l. |

(1) CFU = Colony-forming unit, PFU = Plaque-forming unit.
(2) d.l. = detection limit (1 CFU for spores and bacteria on supports, 60 CFU for spores and bacteria in flakes, 20 PFU for viral particles on supports and 10 PFU for viral particles in flakes).

Example 14

In this example, the biocidal efficiency of the gel according to the invention is evaluated on two bacterial strains B.a. and Y.p. under extreme conditions of temperature, i.e. 5° C. and 50° C. on the same materials as in Example 13. The procedure is the same as the one of the previous example except for the drying conditions of the gel which are the following:

for the tests at 5° C., the drying of the gel is carried out in a cold room for 24 h (the supports are placed in closed containers in order to avoid contamination of the cold chamber). Next, the dishes are placed under MSS at room temperature for completing the drying (since at 5° C., it takes an infinite time to dry the gel without any ventilation, in a closed chamber).

for the tests at 50° C., the coupons in their Petri dish are placed in an oven during the drying of the gel. The dishes were slightly opened.

It should be noted that the drying of the contamination on the supports, prior to the application of the gel, is accomplished under MSS at room temperature.

The results are shown in Table 3.

As regards the drying conditions at 5° C., it is seen that on the support and flake side, no residual contamination is detectable. The extended drying of the gel, related to the low temperature conditions, reinforces the decontamination power of the gel. As regards the drying conditions at d 50° C., the gel takes about 3 h30 to be totally dried. At this temperature, on the support sides, decontamination is total on almost the whole of the coupons, except for a slight residual contamination on a ceramic support. On the solid residue side, slight residual contaminations are detectable in certain cases. In any event, as regards the bacteria, supports and flakes are totally sound. For the spores, which are much more resistant micro-organisms, decontamination of the supports is fully satisfactory, either by annihilation of the spores, or by their transfer into the gel phase.

This example gives the possibility of showing that the gel remains efficient over a wide amplitude of temperature conditions. Whether this is at high or low temperature, the supports are globally very well contaminated, and this from an initial contamination exceeding $10^6$ CFU in most of the cases.

TABLE 3

Efficiency of the biocidal gel on pathogenic agents for extreme temperatures.

| Agent | Support | Temperature (° C.) | Initial contamination of the support (CFU) | Final contamination of the support (CFU) | Residual contamination of the flakes (CFU) |
|---|---|---|---|---|---|
| B. anthracis (spores) | Stainless steel | 5 | $9.3.10^6$ | < d.l. | < d.l. |
| | | 50 | $6.3.10^6$ | < d.l. | 72 |
| | RATP ceramic | 5 | $3.2.10^6$ | < d.l. | < d.l. |
| | | 50 | $2.4.10^6$ | 5 | 276 |
| Y. pestis (bacteria) | Stainless steel | 5 | $3.5.10^5$ | < d.l. | < d.l. |
| | | 50 | $2.8.10^3$ | < d.l. | < d.l. |
| | RATP ceramic | 5 | $8.9.10^4$ | < d.l. | < d.l. |
| | | 50 | $1.6.10^4$ | < d.l. | < d.l. |

Example 15

In this example, the efficiency of the biocidal gel according to the invention is shown on Y.p. under worsened dirt conditions of the supports. In other words, in this example, it is shown that the biological decontamination gel GB79 according to the invention is efficient on dirtied supports. The test procedure is similar to that of example 13, except for the supports which are dirtied beforehand with a brush, with a mixture of 1% of clay of the montmorillonite type, 10% of engine oil 10W40 and 89% of ethanol, and this before applying the contaminant on its surface. Only the contamination with plague is tested.

The results are shown in Table 4. It is seen that the degreasing and decontaminating effect of the gel according to the invention is sufficient for removing bacterial biological dirt and contamination on the support.

TABLE 4

Efficiency of the biocidal gel on pathogenic agents on dirtied supports.

| Agent | Support | Temperature (° C.) | Initial contamination of the support | Final contamination of the support | Residual contamination of the flakes |
|---|---|---|---|---|---|
| Y. pestis (bacteria) | Dirty stainless steel | ~20 | $7.9.10^6$ | < d.l. | < d.l. |
|  | Dirty RATP ceramic | ~20 | $1.6.10^7$ | < d.l. | < d.l. |

Conclusion from all of the Examples:

With regards to Examples 12 to 15 but also 1 to 11, it appears that the alkaline and oxidizing biological decontamination gel according to the invention, is an efficient tool against pathogenic biological contaminants present on various infrastructures subsequent to accidental or malicious biological dissemination.

Annex 1.

Cytotoxicity Test Procedure:

The cytotoxicity test used is illustrated in FIGS. 20 and 21. Human cells HeLa are cultivated at 37° C. in an atmosphere containing 5% of $CO_2$ on cultivation flasks of 150 cm² in DMEM (Dulbecco's Modified Eagle Medium) medium containing 100 U/mL of penicillin and 100 µg/mL of streptomycin.

The cells are shown at a density of 50,000 cells per well in 96-well plates with a solid scintillator bottom Cytostar-T (Perkin-Elmer). The cells (150 µL in complete DMEM: DMEM+10% of foetal calf serum, FCS) are added into each well of the microplate. The complete medium added with toxin (50 µL) is then added to each well. As a general rule, a different ricin concentration is used per row. After incubation for 20 h, the medium (200 µL) is removed and replaced with a DMEM medium without any leucine (Eurobio) containing 10% of FCS and 0.5 µCi/mL of $^{14}C$-leucine (GE). After incubation for 6 h at 37° C., incorporation of radioactivity by the cells is determined by reading plates with a scintillation counter Wallac 1450 microbeta trilux (PE) (FIG. 20).

As these toxins block the synthesis of proteins, the affected cells are no longer capable of incorporating radio-labeled leucine. On the other hand, the cells not treated with ricin or with very low concentrations of ricin ($10^{-14}$-$10^{-16}$ M) still synthesize proteins and therefore incorporate the radio-labeled amino acid. As the cells concentrate the radio-element sufficiently close to the bottom of the well, this causes excitation of the scintillator contained in the plates and leads to the emission of photons detected by the scintillation counter (measurement in counts per minute, cpm). These data are then expressed as a percentage of protein synthesis by the cells. The cytotoxicity curves may thus be traced and the EC50 determined (FIG. 21).

REFERENCES

[1] CUER F., FAURE S. "*Gel de décontamination biologique et procédé de décontamination de surfaces utilisant ce gel*," FR-A1-2962046 and WO-A1-2012/001046.

[2] HOFFMAN D., McGUIRE R. "*Oxidizer gels for detoxification of chemical and biological agents*", U.S. Pat. No. 6,455,751.

[3] HARPER B., LARSEN L. "*A comparison of decontamination technologies for biological agents on selected commercial surface materials*", Biological weapons improved response program, April 2001.

[4] FAURE S., FOURNEL B., FUENTES P., LALLOT Y. "*Procédé de traitement d'une surface par un gel de traitement, et gel de traitement*", FR-A1-2 827 530.

[5] FAURE S., FUENTES P., LALLOT Y. "*Gel aspirable pour la décontamination de surfaces et utilisation*", FR-A1-2 891 470.

The invention claimed is:

1. A biological decontamination gel, consisting of a colloidal solution comprising:
   5% to 30% by mass, based on the mass of the gel, of at least one inorganic viscosifying agent;
   an active biological decontamination agent consisting of the combination of a mineral base selected from hydroxides of alkaline metals and mixtures thereof, and of an oxidizing agent stable in a basic medium selected from permanganates, persulfates, ozone, hypochlorites, and mixtures thereof; the mineral base being present in an amount from 0.05 to 10 mol/L of gel, and the oxidizing agent stable in a basic medium being present in an amount from 0.05 to 5 mol/L of gel;
   optionally 0.1% to 2% by mass based on the mass of the gel, of at least one surfactant;
   and the balance of solvent;
   and the gel not containing any super-absorbent polymer.

2. The gel according to claim 1, wherein the mineral base is selected from sodium hydroxide, potassium hydroxide, and mixtures thereof, and the oxidizing agent stable in a basic medium is selected from hypochlorites, and mixtures thereof.

3. The gel according to claim 2, wherein the active biological decontamination agent consists of the combination of soda and sodium hypochlorite.

4. The gel according to claim 1, wherein the inorganic viscosifying agent is selected from oxides of metals, oxides of metalloids except for silica, hydroxides of metals, hydroxides of metalloids, oxyhydroxides of metals, oxyhydroxides of metalloids, aluminosilicates, clays, and mixtures thereof.

5. The gel according to claim 4, wherein the inorganic viscosifying agent consists of one or several alumina(s).

6. The gel according to claim 5, wherein the alumina(s) represent(s) from 5% to 30% by mass, based on the total mass of the gel.

7. The gel according to claim 1, wherein the surfactant is selected from non-ionic surfactants.

8. The gel according to claim 7, wherein the non-ionic surfactants are selected from block copolymers, ethoxylated fatty acids, and mixtures thereof.

9. The gel according to claim 8, wherein the block copolymers are block copolymers of ethylene oxide and propylene oxide.

10. The gel according to claim 1, wherein the solvent is selected from water, organic solvents and mixtures thereof.

11. The gel according to claim 1, which further comprises at least one mineral pigment.

12. A method for biological decontamination of a surface of a solid substrate contaminated with at least one biological species found on said surface, wherein at least one cycle is carried out comprising the following successive steps:
   a) applying the gel according to claim 1 on said surface;
   b) maintaining the gel on the surface for at least a sufficient duration so that the gel destroys and/or inactivates and/or absorbs the biological species, and so that the gel dries and forms a dry and non-powdered solid residue possibly containing said biological species;
   c) removing the dry and solid residue possibly containing said biological species.

13. The method according to claim 12, wherein the substrate is made of at least one material selected from metals; alloys; stainless steel; painted steels; polymers; glasses; cements; mortars and concretes; plasters; bricks; natural or artificial stone; and ceramics.

14. The method according to claim 13, wherein the polymers are selected from plastics and rubbers.

15. The method according to claim 14, wherein the plastics or rubbers are selected from poly(vinyl chloride)s; polypropylenes; polyethylenes; high density polyethylene; poly(methyl methacrylate)s; poly(vinylidene fluoride)s; polycarbonates.

16. The method according to claim 12, wherein the biological species is selected from among bacteria, fungi, yeasts, viruses, toxins, spores, prions and protozoa.

17. The method according to claim 16, wherein the biological species is selected from biotoxic species.

18. The method according to claim 17, wherein the biotoxic species are selected from pathogenic, toxins, bacteria, and viruses.

19. The method according to claim 18, wherein the pathogenic spores are spores of *Bacillus anthracis*.

20. The method according to claim 18, wherein the toxins are selected from the group consisting of botulinic toxin and ricin.

21. The method according to claim 18, wherein the bacteria are Yersinia pestis bacteria.

22. The method according to claim 18, wherein the viruses are selected from the group consisting of viruses of vaccinia and viruses of hemorrhagic fevers.

23. The method according to claim 12, wherein the gel is applied on the surface in an amount from 100 g to 2,000 g of gel per $m^2$ of surface.

24. The method according to claim 12, wherein the gel is applied on the solid surface by spraying, with a brush, or with a trowel.

25. The method according to claim 12, wherein during step b), the drying is carried out at a temperature from 1° C. to 50° C., and under relative humidity from 20% to 80%.

26. The method according to claim 12, wherein the gel is maintained on the surface for a period from 2 to 72 hours.

27. The method according to claim 12, wherein the dry and solid residue appears as particles with a size from 1 to 10 mm.

28. The method according to claim 12, wherein the dry and solid residue is removed from the solid surface by brushing and/or suction.

29. The method according to claim 12, wherein the described cycle is repeated from 1 to 10 times by using the same gel during all the cycles or by using different gels during one or several cycle(s).

30. (Withdrawn-previously presented) The method according to claim 10, wherein, during step b), the gel, before total drying, is re-wetted with the solution of the gel applied during step a) in the solvent thereof.

* * * * *

UNITED STATES PATENT AND TRADEMARK OFFICE
CERTIFICATE OF CORRECTION

PATENT NO. : 10,251,391 B2
APPLICATION NO. : 14/780756
DATED : April 9, 2019
INVENTOR(S) : Amélie Ludwig et al.

Page 1 of 1

It is certified that error appears in the above-identified patent and that said Letters Patent is hereby corrected as shown below:

In the Specification

Column 21, Line 45, "1004" should read --100µL--.

In the Claims

Column 36, Line 35, "30. (Withdrawn-previously presented) The method according to claim 10, wherein, during step b), the gel, before total drying, is re-wetted with the solution of the gel applied during step a) in the solvent thereof." should read --30. The method according to claim 12, wherein, during step b), the gel, before total drying, is re-wetted with the solution of the gel applied during step a) in the solvent thereof.--.

Signed and Sealed this
Thirtieth Day of July, 2019

Andrei Iancu
*Director of the United States Patent and Trademark Office*